US006451549B1

(12) United States Patent
Escher et al.

(10) Patent No.: US 6,451,549 B1
(45) Date of Patent: Sep. 17, 2002

(54) SECRETED RENILLA LUCIFERASE

(75) Inventors: Alan P. Escher, Redlands; Jingxue Liu, Loma Linda, both of CA (US)

(73) Assignee: Loma Linda University, Loma Linda, CA (US)

( * ) Notice: Subject to any disclaimer, the term of this patent is extended or adjusted under 35 U.S.C. 154(b) by 0 days.

(21) Appl. No.: 09/808,589

(22) Filed: Mar. 14, 2001

Related U.S. Application Data

(63) Continuation of application No. PCT/US99/20093, filed on Sep. 2, 1999, and a continuation of application No. 09/330,317, filed on Jun. 10, 1999, now Pat. No. 6,228,604.
(60) Provisional application No. 60/099,214, filed on Sep. 4, 1998.

(51) Int. Cl.[7] ............................. C12Q 1/26; C12N 9/02; C12N 1/21; C12N 15/52; C07H 21/04
(52) U.S. Cl. ....................... 435/25; 435/189; 435/252.3; 435/325; 435/320.1; 435/349; 435/350; 435/351; 435/352; 435/353; 435/354; 536/23.2; 536/23.4; 536/23.5
(58) Field of Search ....................... 435/25, 189, 252.3, 435/325, 320.1, 349–354; 536/23.2, 23.4, 23.5

(56) References Cited

U.S. PATENT DOCUMENTS

| | | | | |
|---|---|---|---|---|
| 5,221,623 | A | 6/1993 | Legocki et al. | 435/252.3 |
| 5,292,658 | A | 3/1994 | Cormier et al. | 435/252.33 |
| 5,418,155 | A | 5/1995 | Cormier et al. | 435/189 |
| 5,541,309 | A | 7/1996 | Prasher | 536/23.2 |

FOREIGN PATENT DOCUMENTS

| | | |
|---|---|---|
| WO | WO9508347 | 3/1995 |
| WO | WO0020619 | 4/2000 |

OTHER PUBLICATIONS

Berger et al., Secreted placental alkaline phosphatase: a powerful new quantitative indicator of gene expression in eukaryotic cells, *Gene,* 66:1–10 (1988).
Inouye et al., "Imaging of luciferase secretion from transformed Chinese hamster ovary cells," *Proc. Natl. Acad. Sci. USA* 89:9584–9587 (Oct. 1992).
Liu et al., "Improved assay sensitivity of an engineered secreted *Renilla luciferase*," *Gene,* 237(1), (1999) Abstract.
Liu et al., "Secretion of Firefly Luciferase in *E–coli,*" *Biotechnology Letters* 15(11):1111–1116 (Nov. 1993).
Liu et al., "Secretion of functional *Renilla reinformis* luciferase by mammalian cells," *Gene* 203:141–148 (1997).
Lorenz et al., "Expression of the *Renilla reinformis* Luciferase Gene in Mammalian Cells," *J. Biolumin Chemilumin,* 11:31–7 (1996).
Lorenz et al., "Isolation and expression of a cDNA encoding *Renilla reinformis* luciferase," Proc. Natl. Acad. Sci. USA, May 15: 88:4438–4442 (1991).
Miller et al., "Improved retroviral vectors for gene transfer and expression," *Biotechniques* Oct.: 7(9) ;980–2, 984–6, 989–90 (1989).
Miller, et al., "Use of Retroviral Vectors for Gene Transfer and Expression," *Meth. in Enz.,* 217:581–99 (1993).
Okano, et al., "Functional Expression of Human Leukocyte Elastase (HLE)/Medullasin in Eukaryotic Cells," *Biochemical and Biophysical Research Communications,* 167(3) :1326–1332 (Mar. 30, 1990).
Sherf et al., "Luciferase Dual–Luciferase™ Reporter Assay: An Advanced Co–Reporter Technology Integrating Firefly and Renilla Luciferase Assays," *Promega Notes* 57 2–9.
Taniguchi et al., "Structure and expression of a cloned cDNA for human interleukin–2," *Nature,* 302:305–310 1983.
Thompson et al., "*Vargula hilgendorfii* luciferase: a secreted reporter enzyme for monitoring gene expression in mammalian cells," *Gene,* 96:257–262 (1990).
Yang, T.T. et al., "Quantification of gene expression with a secreted alkaline phosphatase reporter system," *Biotechniques,* 23:1110–1114 (1997).

*Primary Examiner*—Elizabeth Slobodyansky
(74) *Attorney, Agent, or Firm*—David A. Farah; Sheldon & Mak

(57) ABSTRACT

A polynucleotide encoding a secreted form of wild type Renilla luciferase. Also provided is a polynucleotide encoding a secreted modified form of wild type Renilla luciferase. Additionally, the polypeptides encoded by the polynucleotides of the present invention and uses of the polynucleotides and polypeptides of the present invention in biological assays. Also, a stable mammalian packaging cell line which produces retroviruses carrying a polynucleotide encoding a secreted Renilla luciferase.

15 Claims, 18 Drawing Sheets

| PERCENTAGE OF CLONES | LUCIFERASE ACTIVITY |
|---|---|
| 15% | 0-10 RLU |
| 56% | 10-100 RLU |
| 18% | 100-500 RLU |
| 3% | 500-1000 RLU |
| 8% | >1000 RLU |

FIG. 18

SECRETED RENILLA LUCIFERASE

CROSS-REFERENCE TO RELATED APPLICATIONS

The present Application is a continuation of international application PCT/US99/20093 filed Sep. 2, 1999, entitled "Secreted Renilla Luciferase," and a continuation of U.S. patent application Ser. No. 09/330,317 filed Jun. 10, 1999, entitled "Secreted Renilla Luciferase now U.S. Pat. No. 6,228,604," and claims the benefit of United States Provisional Patent Application 60/099,214 filed Sep. 4, 1998, entitled "Secreted Renilla Luciferase"; the contents of which are incorporated by reference herein in their entirety.

STATEMENT REGARDING FEDERALLY SPONSORED RESEARCH OR DEVELOPMENT

This invention was made with Government support under cooperative agreement number DAMD17-97-2-6017 with the United States Department of the Army, United States Army Research Acquisition Activity. The Government has certain rights in this invention.

BACKGROUND

Genes encoding proteins with readily detectable activities, referred to as reporter proteins, are routinely used in biological assays to study a variety of biological events. These biological events include gene expression, gene transfer and the intracellular movement of molecules. Genes encoding reporter proteins which are capable of generating light emission such as luciferases, in particular, have been incorporated into sensitive, noninvasive biological assays which are simple to perform. The most widely used luciferases used in assays are encoded by genes from the biolumninescent Vibrio bacteria, the jellyfish *Aequoria victoria*, and the firefly *Photinus pyralis*.

Further, genes encoding reporter proteins that are secreted offer distinct advantages when they are incorporated into assays because they permit the monitoring of gene expression over time without destroying the cells or tissues which are being studied. Secreted alkaline phosphatase (SEAP) is an example of a light-emitting, secreted reporter protein whose encoding gene is useful in mammalian cell assays (see, for example, Yang, T. T. et al. "Quantification of gene expression with a secreted alkaline phosphatase reporter system." *Biotechniques*, 23: 1110–1114 (1997)). Other light-emitting, secreted reporter proteins are known, including the luciferase from the marine ostracod *Vargula hilgendorfii*, or from the decapod shrimp Oplophorus, but their use is restricted because either the luciferin substrates for their secreted proteins are not commercially available or their encoding genes have not been cloned.

Additionally, dual reporter assay systems are often used for studies of gene expression in transiently transfected cells. In these systems, one reporter gene is fused to a DNA promoter element of interest, while the other reporter gene is fused to a constitutive promoter. Measurements obtained from the expression of the latter are then taken for normalization between experiments. A good dual reporter system should offer assays that are both sensitive and simple to perform.

Therefore, it would be useful to have other genes encoding secreted reporter proteins which could be incorporated into biological assays and which have commercially available substrates for the secreted reporter proteins they encode. Further, it would be useful to have vectors containing these genes to prepare kits for performing the assays. Additionally, it would be useful to have a dual reporter system that is both sensitive and simple to perform.

SUMMARY

In one embodiment, there is provided a polynucleotide encoding a secreted Renilla luciferase. According to another embodiment of the present invention, there is provided a secreted Renilla luciferase.

According to still another embodiment of the present invention, there is provided a method of performing a biological assay. The method comprises providing a polynucleotide encoding a secreted Renilla luciferase. The method can additionally comprise transfecting a host cell, such as a mammalian cell, with the polynucleotide. The method can also comprise detecting light emission from the Renilla luciferase coded by the polynucleotide that has been secreted in the culture media in which the host cell is growing. The method can further comprise transfecting the host cell with a second polynucleotide encoding a second light emitting protein such as seap. The method can also comprise detecting light emission from the second light emitting protein coded by the second polynucleotide that has been secreted in the culture media.

According to another embodiment of the present invention, there is provided a plasmid or a vector containing a polynucleotide according to the present invention, as well as a host cell, such as a mammalian cell, transfected with a polynucleotide according to the present invention. The present invention can also include a kit for performing a biological assay, comprising a polynucleotide according to the present invention. The kit can include a second polynucleotide, such as seap.

According to another embodiment of the present invention, there is provided a stable mammalian packaging cell line which produces retroviruses carrying a polynucleotide encoding a secreted Renilla luciferase.

FIGURES

These and other features, aspects and advantages of the present invention will become better understood with regard to the following description, appended claims, and accompanying figures where:

Figure 10:
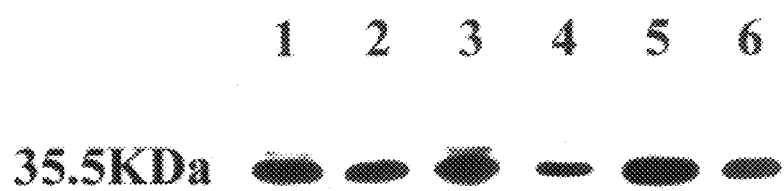
Figure 11:
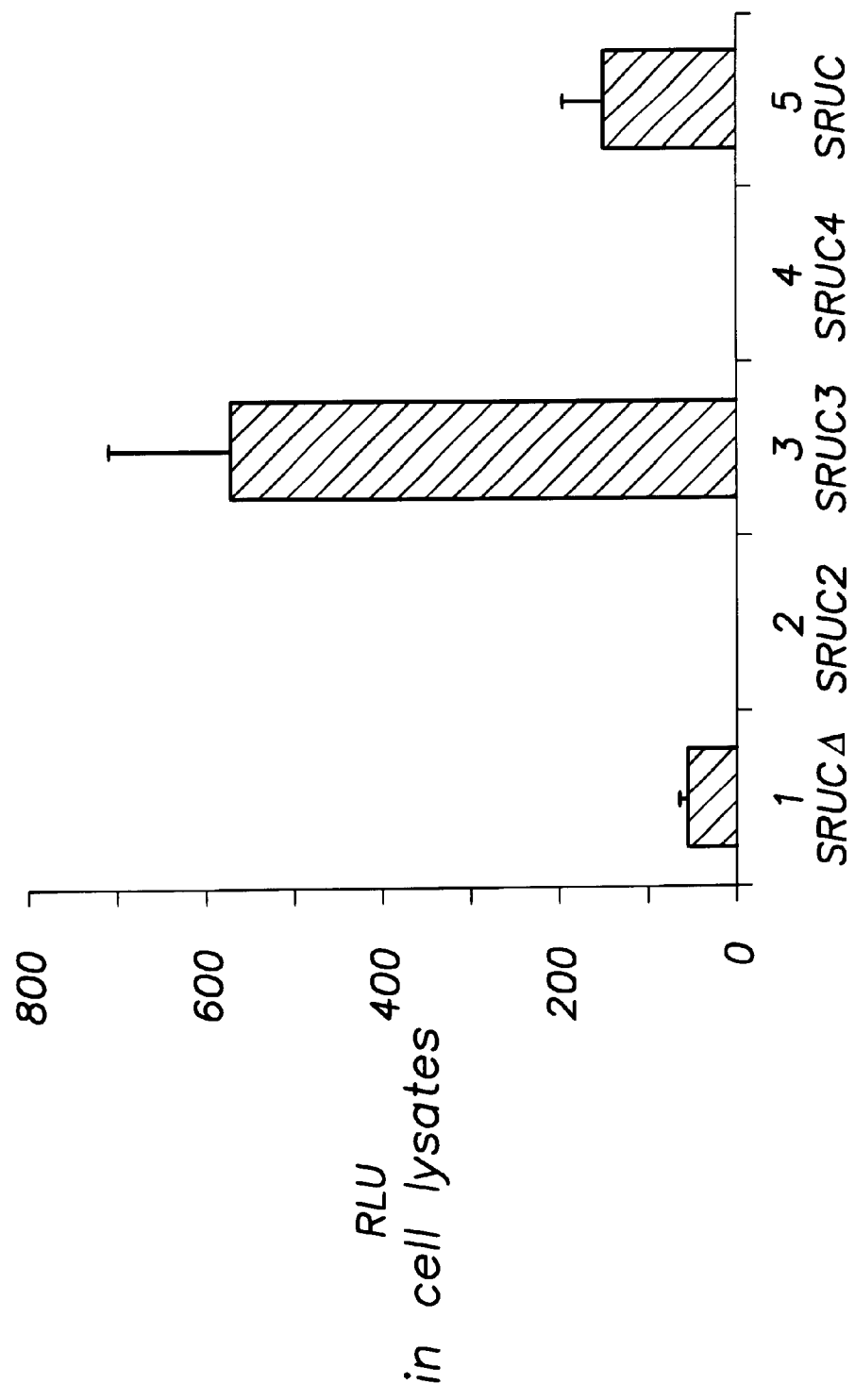
Figure 12:
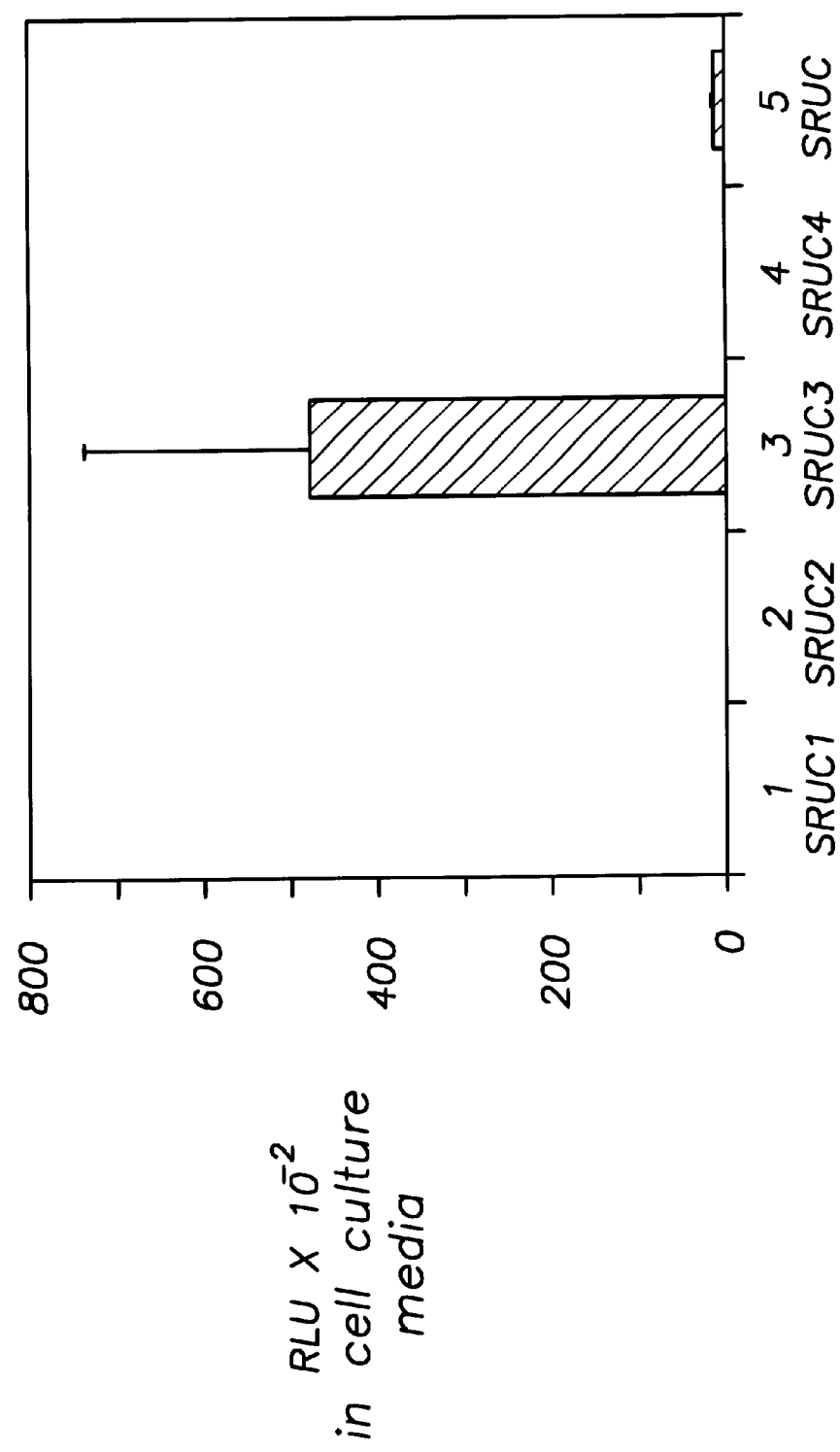
Figure 13:
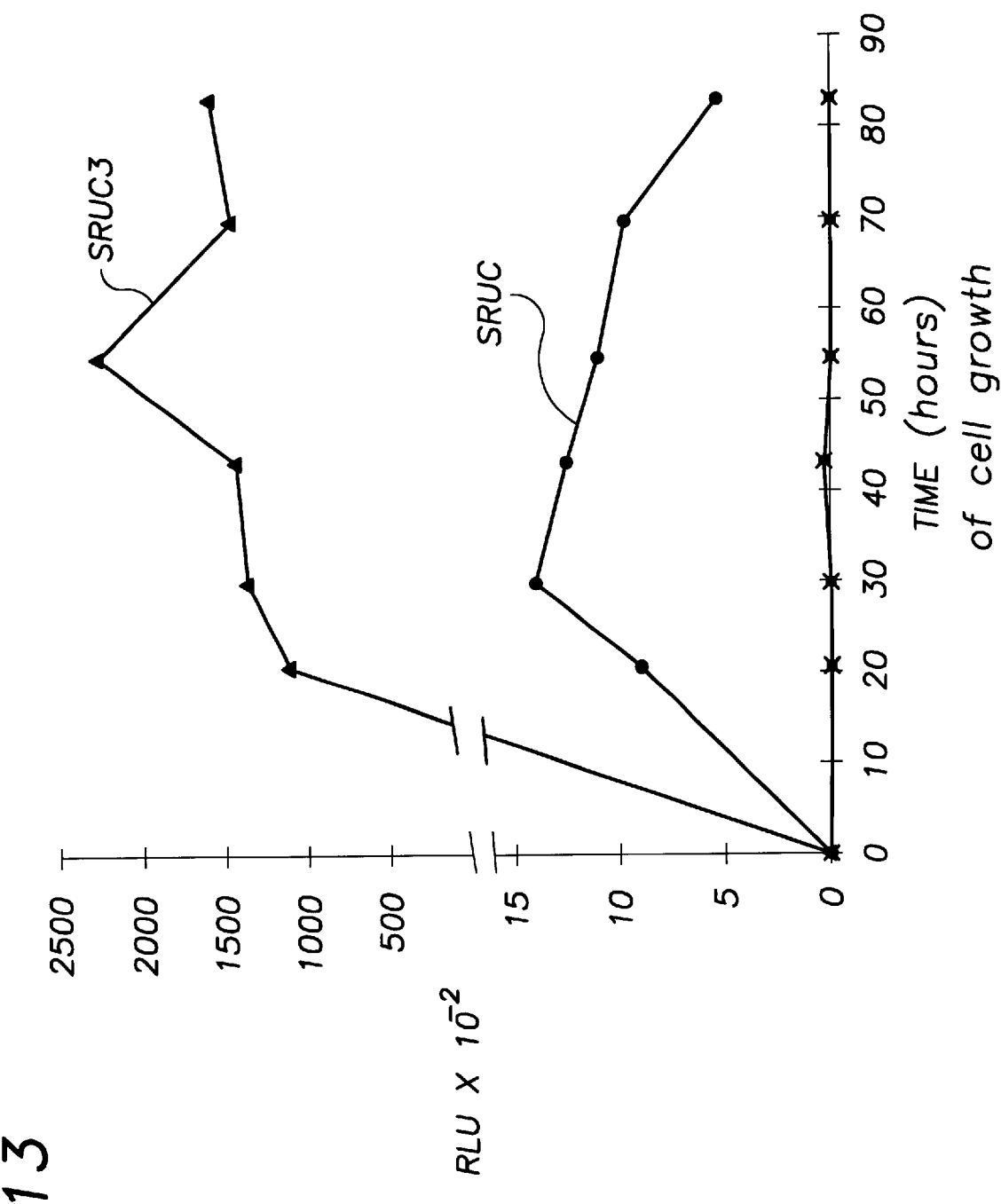
Figure 14:
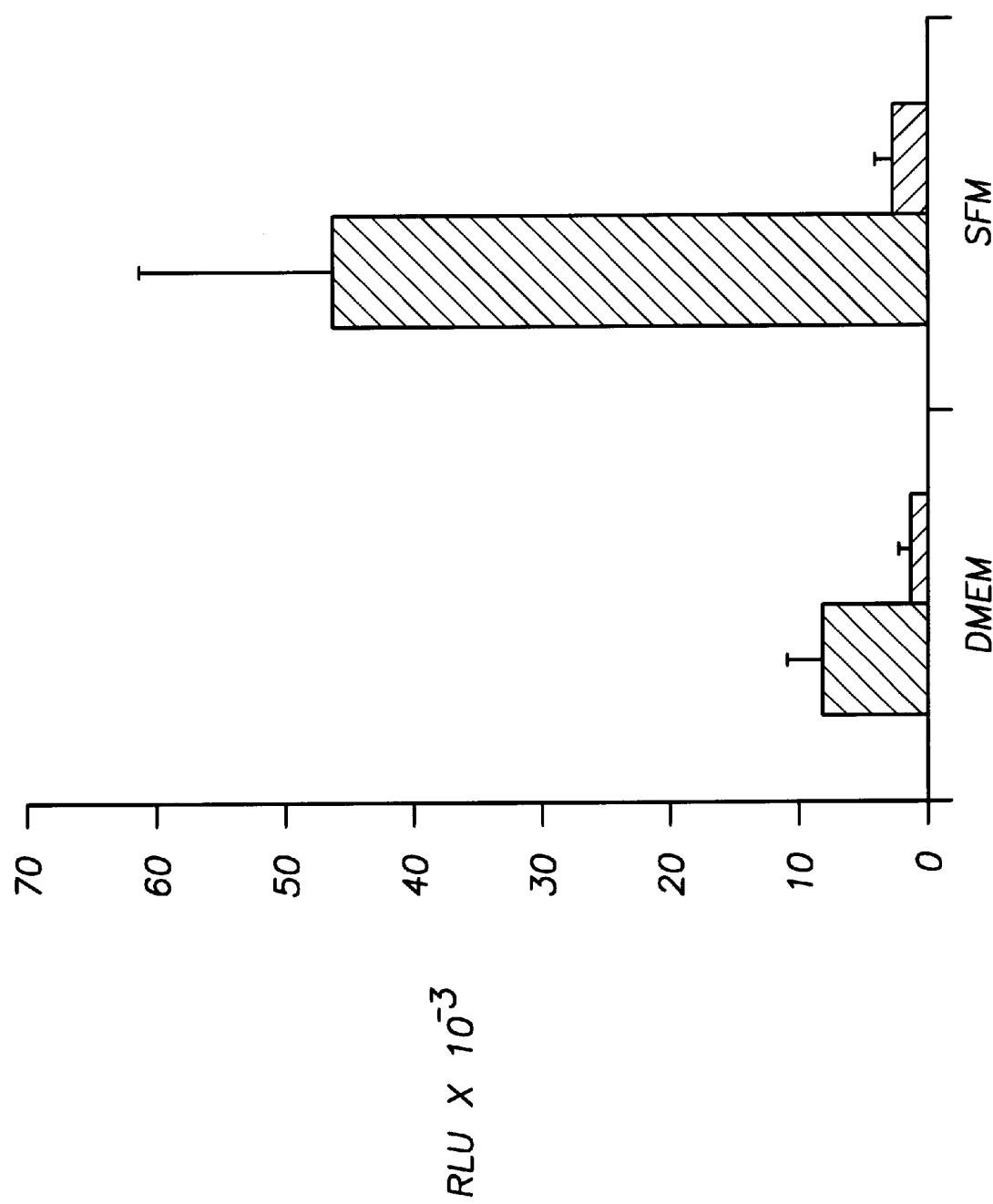
Figure 15:
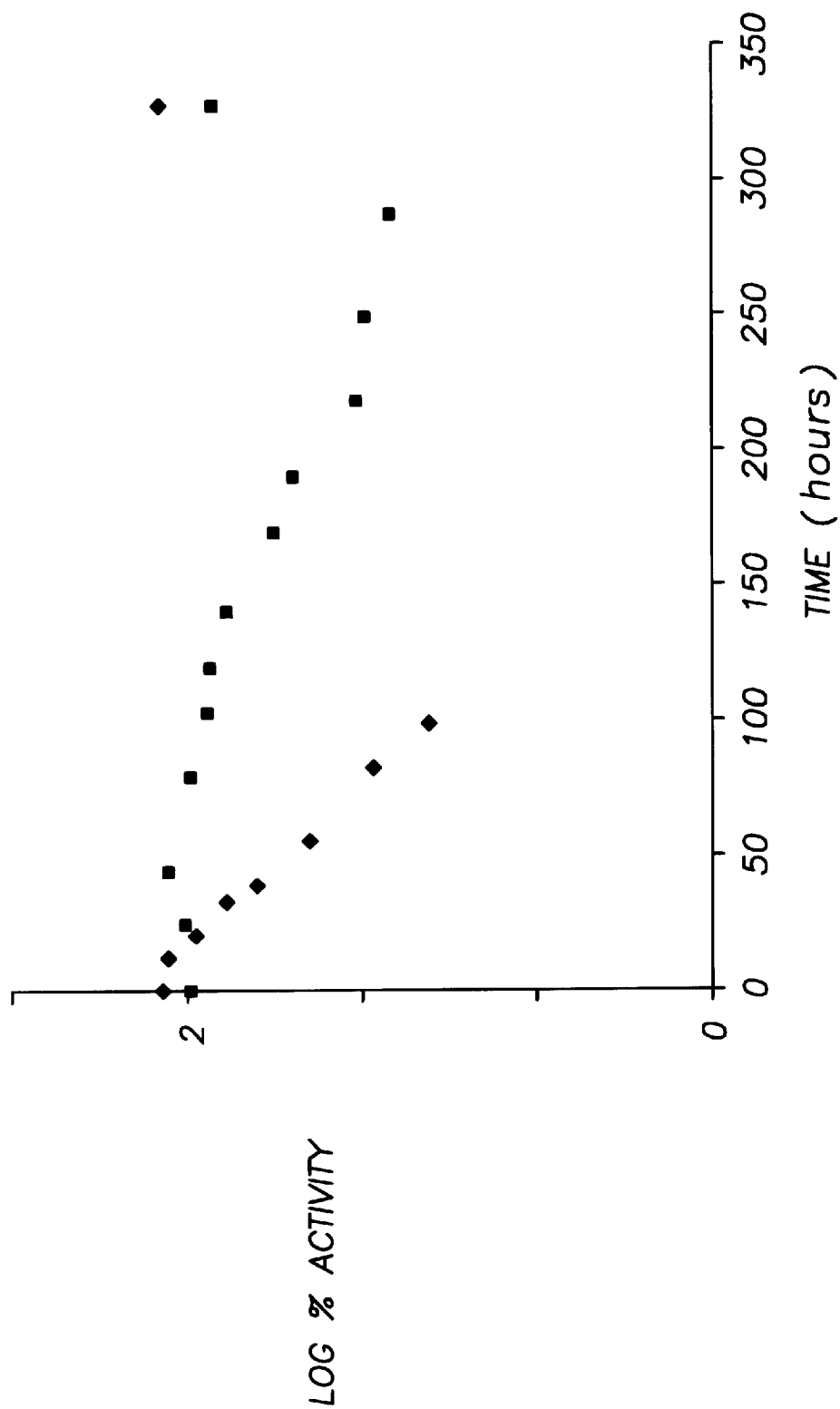
Figure 16:
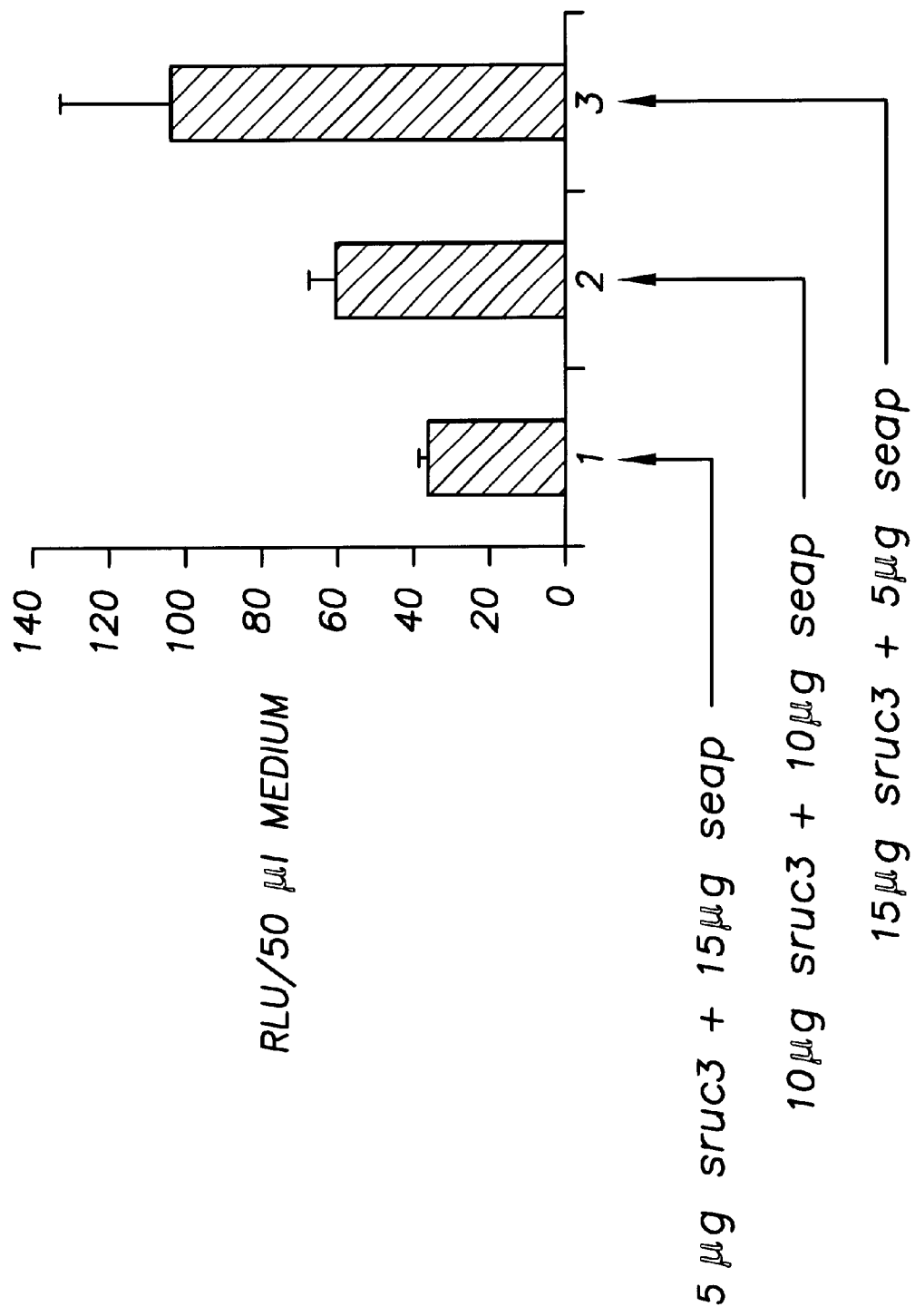
Figure 17:
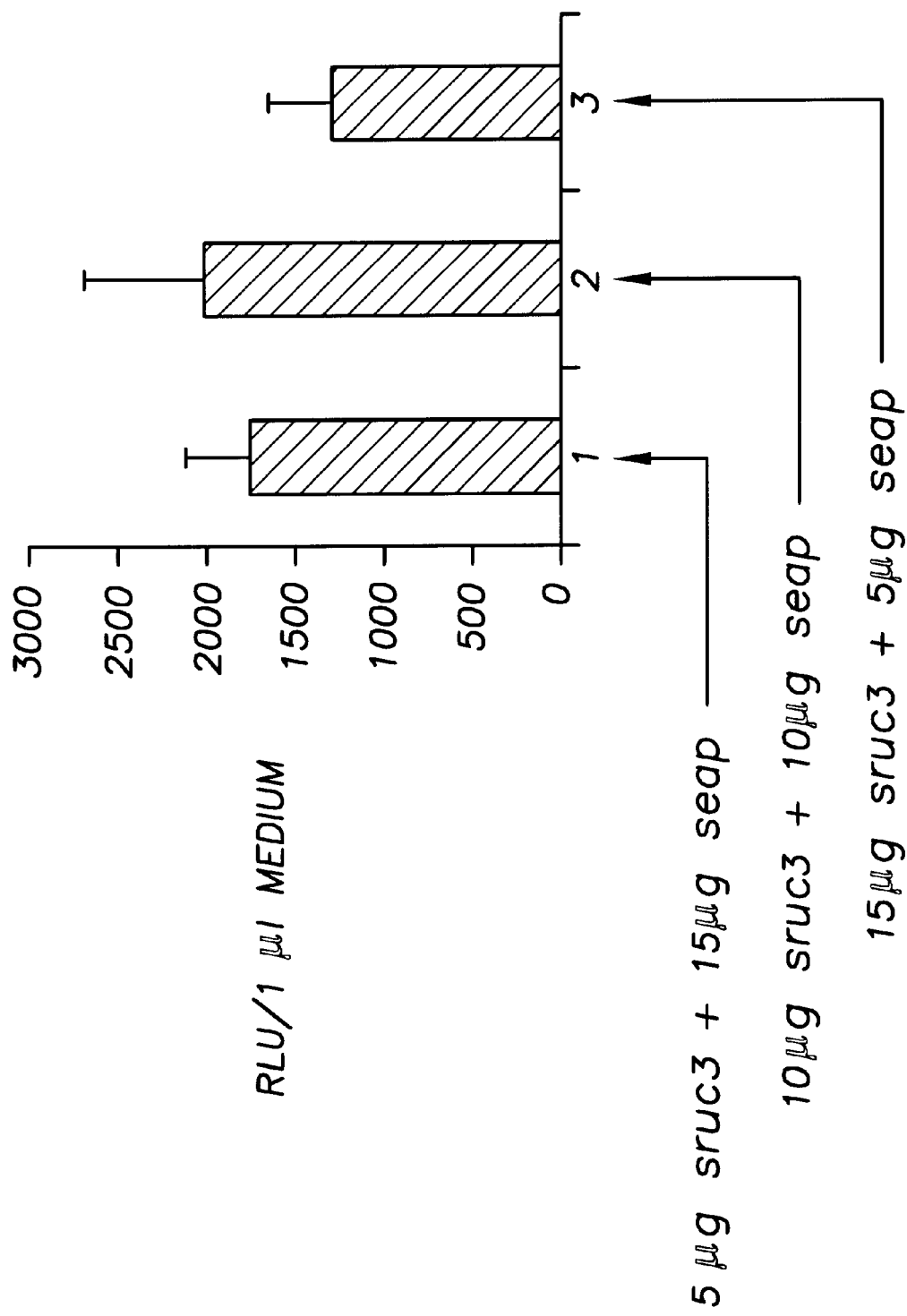

FIG. 10 shows an immunoblot analysis for the presence of Renilla luciferase in total cell lysates of mammalian cells transfected with expressing genes encoding SRUC (lane 1), SRUC1 (lane 2), SRUC2 (lane 3), SRUC3 (lane 4), and SRUC4 (lane 5), and isolated from *Escherichia coli* expressing the Renilla luciferase cDNA as control (lane 6);

FIG. 11 shows a bar graph depicting the measured Renilla luciferase bioluminescence activity in mammalian cell lysates for cells transfected with SRUC1 (lane 1), SRUC2 (lane 2), SRUC3 (lane3), SRUC4 (lane 4) and SRUC (lane 5);

FIG. 12 shows a bar graph depicting the measured Renilla luciferase bioluminescence activity in culture media of cells transfected with SRUC1 (lane 1), SRUC2 (lane 2), SRUC3 (lane3), SRUC4 (lane 4) and SRUC (lane 5);

FIG. 13 shows a graph of the time course appearance of Renilla luciferase activity in cell culture media of mammalian cells transfected with pND2-SRUC, pND2-SRUC1, pND2-SRUC2, pND2-SRUC3, and pND2-SRUC4;

FIG. 14 shows a bar graph of the Renilla luciferase activity for cell lysates and culture medium of cells grown in DMEM supplemented with 10% FBS and cells grown serum free medium supplemented with 1% FBS;

FIG. 15 shows a graph of stability of bioluminescence activity of SRUC and SRUC3 that has already been secreted by mammalian cells;

FIG. 16 shows a bar graph of the luciferase activity in culture medium of cells co-transfected with sruc3 and seap;

FIG. 17 shows a bar graph of the alkaline phosphatase activity in culture medium of cells co-transfected with sruc3 and seap; and FIG. 18 shows a chart of the range of Renilla luciferase activities measured in the culture media of stable packaging cell lines transduced with retroviruses carrying the sruc3 gene.

DESCRIPTION

*Renilla reniformis* is an anthozoan coelenterate living in shallow coastal waters of North America which displays blue-green bioluminescence. This bioluminescence results from a monomeric luciferase enzyme ($M_r$ 36,000) which catalyzes the oxidative decarboxylation of the complex organic molecule coelenterazine (the luciferin) in the presence of dissolved oxygen to yield oxyluciferin, $CO_2$, and blue light ($\lambda_{max}$=480 mn) in vitro. In vivo, the *R. reniformis* energy transfer occurs from the luciferase-bound oxyluciferin excited state donor to a green fluorescent protein acceptor resulting in blue-green light emission ($\lambda_{max}$=509 nm). A polynucleotide sequence, SEQ ID NO:1, encoding a functional full-length Renilla luciferase protein SEQ ID NO:2 has been cloned (Lorenz et al., "Isolation and expression of a cDNA encoding *Renilla reniformis* luciferase." *Proc. Natl. Acad. Sci. USA*, May 15; 88(10):4438–4442 (1991)).

According to one embodiment of the present invention, there is provided a polynucleotide sequence encoding a naturally occurring light-emitting reporter protein which has an amino acid sequence added so that it is secreted by mammalian cells. According to another embodiment of the present invention, there is provided a polynucleotide sequence encoding a modified form of a naturally occurring light-emitting reporter protein which additionally has an amino acid sequence added so that it is secreted by mammalian cells. The invention also includes the secreted light-emitting reporter proteins which are encoded by the polynucleotides of the present invention. The invention further includes methods of using the polynucleotides and polypeptides of the present invention, and kits containing the polynucleotides of the present invention which can be used to perform biological assays of biological events such as gene expression, gene transfer and the intracellular movement of molecules within multicellular organisms, among other biological events.

In a preferred embodiment, the invention includes a plurality of modified luciferase genes from *Renilla reniformis*. When expressed in mammalian cells, one of these polynucleotides, designated sruc, encodes wild type *R. reniformis* luciferase, designated SRUC, which has an amino acid sequence added so that it is secreted by mammalian cells. Advantageously, this protein is functional and its substrate is commercially available, making the secreted form of this reporter protein suitable for routine use in biological assays. When expressed in mammalian cells, another of these polynucleotides, designated sruc3, encodes a modified form of wild type *R. reniformis* luciferase, designated SRUC3, which also has an amino acid sequence added so that it is secreted by mammalian cells. SRUC3 has improved bioluminescence activity and increased stability over SRUC.

Besides being used in a biological assay system alone, at least one of the polynucleotides of the present invention can be used in conjunction with the seap gene in a dual reporter assay system for gene expression and for other biological events in cells, including mammalian cells. Further, at least one of the polynucleotides of the present invention can be used to make stable mammalian packaging cell lines which produce retroviruses carrying the polynucleotide. Additionally, at least one of the polynucleotides of the present invention can be used as a marker gene for retroviral gene transfer experiments.

I. PRODUCTION AND EXPRESSION OF A POLYPEPTIDE WHICH ENCODES A SECRETED FORM OF WILD TYPE RENILLA LUCIFERASE

Figure 1:
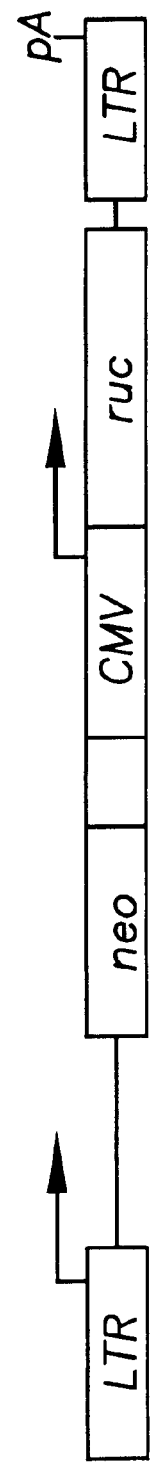
FIG. 1 shows a partial schematic diagram of the plasmid pLNCX-RUC.

A. Construction of Plasmids Encoding Wild Type Renilla Luciferase Preprotein Gene First, a plasmid containing the cDNA encoding wild type Renilla luciferase was constructed as follows. The gene, SEQ ID NO:1, GenBank accession number M63501, encoding wild type Renilla luciferase SEQ ID NO:2, was ligated as a 975 bp EcoRV-SmaI DNA fragment from plasmid pBluescript II KS(+) carrying the luciferase gene into the HpaI site of plasmid pLNCX (GenBank accession number M28247), generating plasmid pLNCX-RUC. Referring now to FIG. 1, there is shown a partial schematic diagram of the plasmid pLNCX-RUC, where "LTR" refers to the long terminal repeat, "neo" refers to the neomycin resistance gene, "CMV" refers to the cytomegalovirus promoter, "ruc" refers to the cDNA encoding wild type Renilla luciferase, and "pA" refers to the polyadenylation site. An ampicillin resistance gene and the bacterial origin of replication are not shown.

B. Construction of Plasmids Encoding a Gene Encoding a Secreted Functional Wild Type Renilla Luciferase Preprotein Next, a plasmid containing the cDNA, SEQ ID NO:3, encoding a secreted functional form of wild type Renilla luciferase preprotein SEQ ID NO:4, pLNCX-SRUC, was constructed as follows. First, an 87 bp DNA fragment, SEQ ID NO:5, was prepared.

SEQ ID NO:5: ATGTACAGGATGCAACTCCTGTCT-TGCATTGCACTAAGT CTTGCACTTGTCACAAA-CAGTGCACCTACTGAATTCAGCTTAA AGATG

SEQ ID NO:5 encoded the 23 amino acid residue signal sequence of human IL-2 protein (IL2SP), GenBank accession number AJ00264, followed by a 5 amino acid linker and by the methionine start codon of wild type Renilla luciferase, ATG, by amplification from human embryonic kidney cell line A293 genomic DNA (Taniguchi et al., "Structure and expression of a cloned cDNA for human interleukin-2." *Nature* 302:305–310 (1983)), using the polymerase chain reaction (PCR) with primers SEQ ID NO:6, and SEQ ID NO:7.

SEQ ID NO:6 TTTGAATTCATGTACAGGATG-CAACTCCT

SEQ ID NO:7 TTTGAATTCAGTAGTGCACT-GTTTGTGAC

PCR was performed using Pwo polymerase (Boehringer-Mannheim, Mannheim, Germany) and thermocycling for 30 cycles at 94° C. for 15 seconds and 50° C. for 30 seconds.

The PCR fragment was cloned directly into vector pGEMT (Promega, Madison, Wis., U.S.), excised using the EcoRI sites introduced by both primers, and ligated 9 bp upstream of the Renilla luciferase gene in plasmid pLXSN-RUC. (Liu et al., "Secretion of functional *Renilla reniformis* luciferase by mammalian cells." *Gene* 203:141–148 (1997)). The correct sequences of the PCR product and of the in-frame fusion of this product with wild type Renilla luciferase gene were confirmed by automated DNA sequencing. The DNA sequence encoding the IL2SP-Renilla luciferase protein fusion was amplified using primers SEQ ID NO:6, and SEQ ID NO:8.

SEQ ID NO:8 TTTCCCGGGAAAAATG-TAAATAAAAAACCA

The PCR product carrying the gene encoding the IL2SP-Renilla luciferase protein fusion (sruc), was then cloned into the plasmid pGEMT and subcloned as a KspI-SmaI fragment into the HpaI site of retroviral vector pLNCX, under transcriptional control of the CMV promoter, generating plasmid PLNCX-SRUC for mammalian cell expression studies, and for future packaging into retroviral particles for introduction into animal model system.

Figure 2:
FIG. 2 shows a partial schematic diagram of the plasmid pLNCX-SRUC comprising residues 14–29 of SEQ ID NO:14.

Referring now to FIG. 2, there is shown a partial schematic diagram of the plasmid pLNCX-SRUC, showing the protein fusion junction, where "LTR" refers to the long terminal repeat, "neo" refers to the neomycin resistance gene, "CMV" refers to the cytomegalovirus promoter, "ruc" refers to the cDNA encoding wild type Renilla luciferase, and "pA" refers to the polyadenylation site. An ampicillin resistance gene and the bacterial origin of replication are not shown. The putative site of cleavage of the signal peptidase is shown by the arrow between residues 20 and 21.

C. Transfection of Cultured Mammalian Cells with Plasmids Encoding the Wild Type Renilla Luciferase Protein Gene and Secreted Wild Type Renilla Luciferase Preprotein Gene Simian COS-7 cells were cultured and transfected with the plasmids pLNCX, pLNCX-RUC, or pLNCX-SRUC as follows. First, the mammalian cells were grown in 100 mm tissue culture plates containing 10 ml DMEM medium (Sigma Chemical, St. Louis, Mo., U.S.) supplemented with 10% fetal bovine serum (FBS) (Biowhittaker, Walkersville, Md., U.S.). The medium was changed 3 hours prior to transfection when cells were 75% confluent.

Each plate of the cultured mammalian cells was transfected with the 40 $\mu$g of plasmid DNA per plate using the ProFection Calcium Phosphate System (Promega), according to the manufacturer's instructions. Six hours after transfection, the cells were washed twice with phosphate-buffered saline (PBS). Then, 10 ml of DMEM medium and 10% FBS were added to each plate. No differences in cell morphology or cell growth were observed between cell expressing the wild type Renilla luciferase gene, and cells expressing the sruc gene, indicating that presence of the sruc gene does not affect cell growth or morphology when compared to cells expressing the ruc gene.

D. Measurement of Renilla Luciferase Stability in Cell Culture Media and in Whole Blood The stability of Renilla luciferase in cell culture media was determined as follows. Three nanograms of purified Renilla luciferase (isolated from an overexpressing *Escherichia coli* strain and lacking IL2SP) was added to a 100 mm plate containing COS-7 cells growing at 75% confluency in 10 ml DMEM supplemented with 10% FBS, and another three nanograms of purified Renilla luciferase was added to a 100 mm plate containing COS-7 cells growing at 75% confluency in 10 ml QBSF 51 supplemented with 1% FBS. The plates were incubated at 37° C. in 5% $CO_2$, and a 200 $\mu$l aliquot of medium was taken at regular time intervals for bioluminescence assay.

The stability of Renilla luciferase in whole blood was determined as follows. Three nanograms of the same isolated Renilla luciferase was added to 700 $\mu$l of freshly obtained whole hamster blood containing 50 $\mu$l of a heparin solution (1000 units/ml, from Elkins-Sinn), and placed at 37° C. A 10 $\mu$l aliquot was taken at regular time intervals, and diluted into 200 $\mu$l assay buffer for bioluminescence assay.

Figure 3:
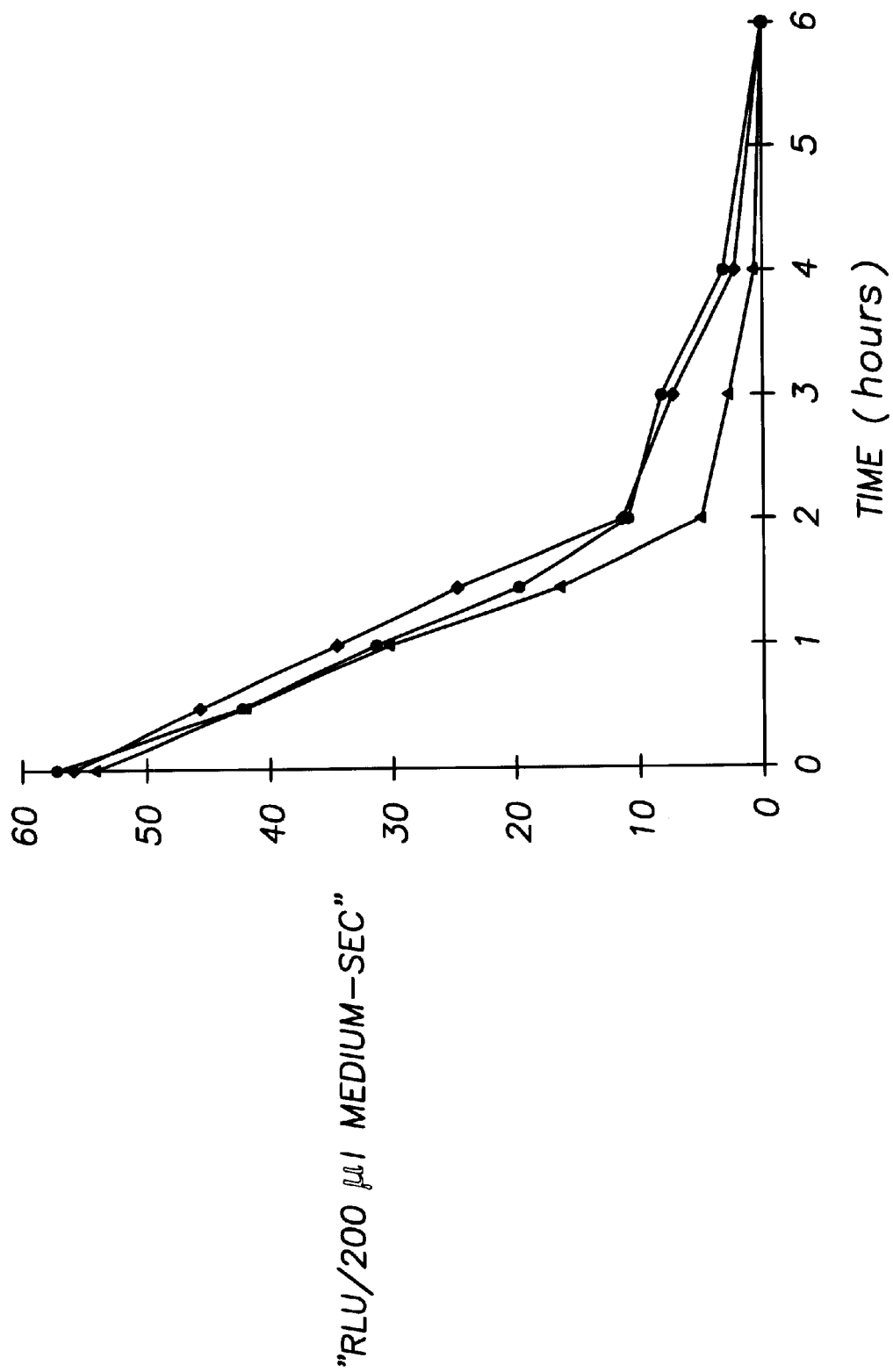
FIG. 3 shows a graph of the stability of isolated Renilla luciferase in cell culture media and in whole blood.

Referring now to FIG. 3, there is shown a graph of the results of these assays. As can be seen, isolated Renilla luciferase lacking IL2SP added to DMEM medium supplemented with 10% FBS (circles), had a half-life of approximately 50 minutes. Isolated Renilla luciferase lacking IL2SP added to QBSF 51 medium supplemented with 1% FBS (diamonds) had a half-life of approximately 57 minutes, indicating that luciferase stability did not vary significantly between these two media. Finally, isolated Renilla luciferase lacking IL2SP added to whole blood (triangles) had a half-life of approximately 36 minutes, an advantageously short half-life for assays to be perform in closed systems. Relative light units (RLU) are shown as per second, per 200 $\mu$l medium.

E. Bioluminescence Assays of Luciferase Activity in Culture Media Containing Secreted Renilla Luciferase and in Cell Lysates of Transfected Mammalian Cells Bioluminescence assays of Renilla luciferase activity was measured from both cell lysates and from the culture media of the mammalian cells transfected with plasmids pLNCX, pLNCX-RUC, or pLNCX-SRUC. In each case, cells from one plate were harvested by scraping in assay buffer containing 0.5 M NaCl, 1 mM EDTA, and 100 mM potassium phosphate, at pH 7.4, 48 hours after transfection, washed once with the assay buffer, resuspended in 1 ml of assay buffer, and then sonicated on ice twice for 10 seconds. Then, 500 $\mu$l of cell lysates in each case were assayed for bioluminescence for 10 seconds using a Turner TD-20e luminometer after rapid injection to ensure even mixing of 500 $\mu$l of 1 $\mu$M coelenterazine hcp (Molecular Probes, Eugene, Oreg. U.S.).

Figure 4:
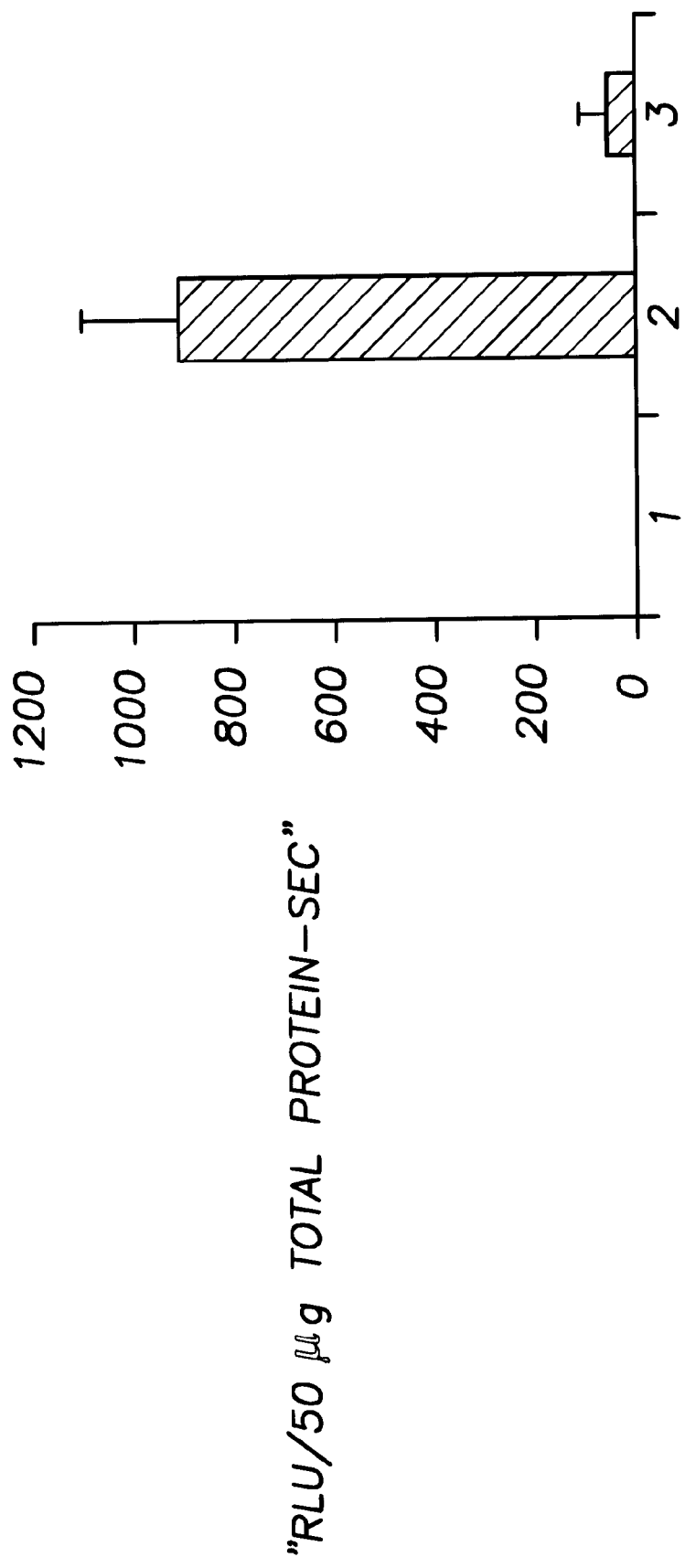
FIG. 4 shows a bar graph of the Renilla luciferase activity in cell lysates for mammalian cells transfected with (1) pLNCX, (2) pLNCX-RUC, or (3) pLNCX-SRUC.
Figure 5:
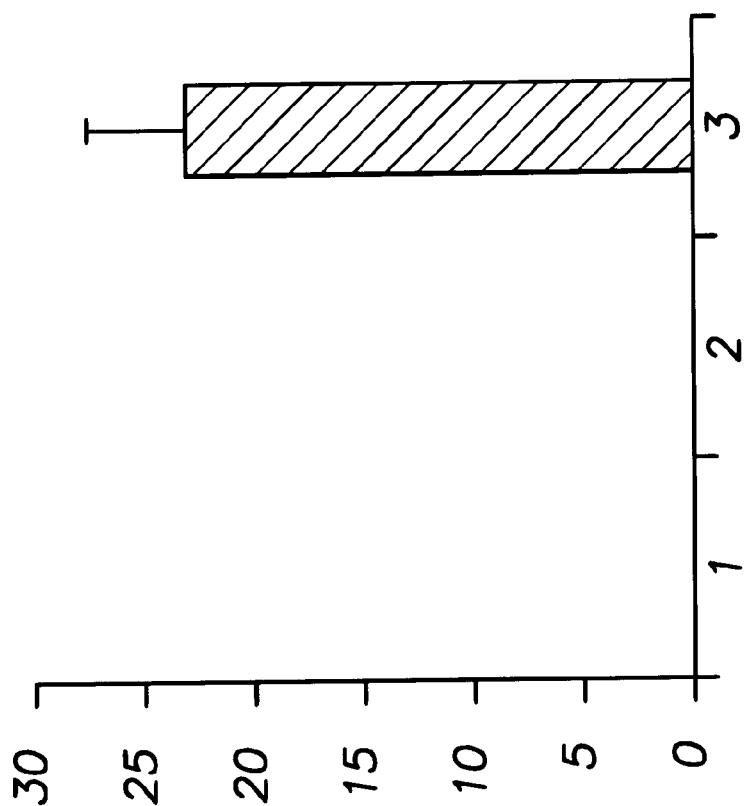
FIG. 5 shows a bar graph of the Renilla luciferase activity in cell culture media of mammalian cells transfected with (1) pLNCX, (2) pLNCX-RUC, or (3) pLNCX-SRUC.

Referring now to FIGS. 4 and 5, there are shown a bar graph of the Renilla luciferase activity in cell lysates and in cell culture media, respectively. Light emission was measured for cells transfected with (1) pLNCX, (2) pLNCX-RUC, or (3) pLNCX-SRUC. Results obtained from six individual transfections are shown. Relative light units (RLU) are show as per second, per 50 μg total protein in FIG. 4 and as per second, per 200 μl medium in FIG. 5.

As can be seen in FIG. 4, Renilla luciferase activity measured from lysates of cells expressing the Renilla luciferase gene construct was approximately 15-times higher than that measured from lysates of cells expressing the sruc gene construct. By contrast, as can be seen in FIG. 5, only cell culture media in which cells expressing the IL2SP-Renilla luciferase gene fusion (sruc) were growing (SRUC medium) contained significant levels of Renilla luciferase activity. Luciferase activity measured in the SRUC medium was not the result of cell lysis, since 10 ml of SRUC medium (DMEM supplemented with 10% FBS) from a 100% confluent 100 mm dish contained, on average, 6000 relative light units (RLU) 48 hours after transfection, while cell lysates from the same culture dish contained, on average, only 600 RLU.

Additionally, the time course of appearance of Renilla luciferase activity in cell culture media was assayed at regular time intervals using the same method on 200 μl aliquots of culture media taken from dishes containing growing the transfected cells. 200 μl of fresh media was added each time to the plates as replacement for the aliquot taken. In one plate containing cells transfected with plasmid pLNCX-SRUC were grown in DMEM medium supplemented with 10% FBS for the first 42 hours, and then grown in QBSF 51 (Sigma) medium supplemented with 1% FBS to investigate the effects of medium composition on accumulation of functional secreted Renilla luciferase.

Figure 6:
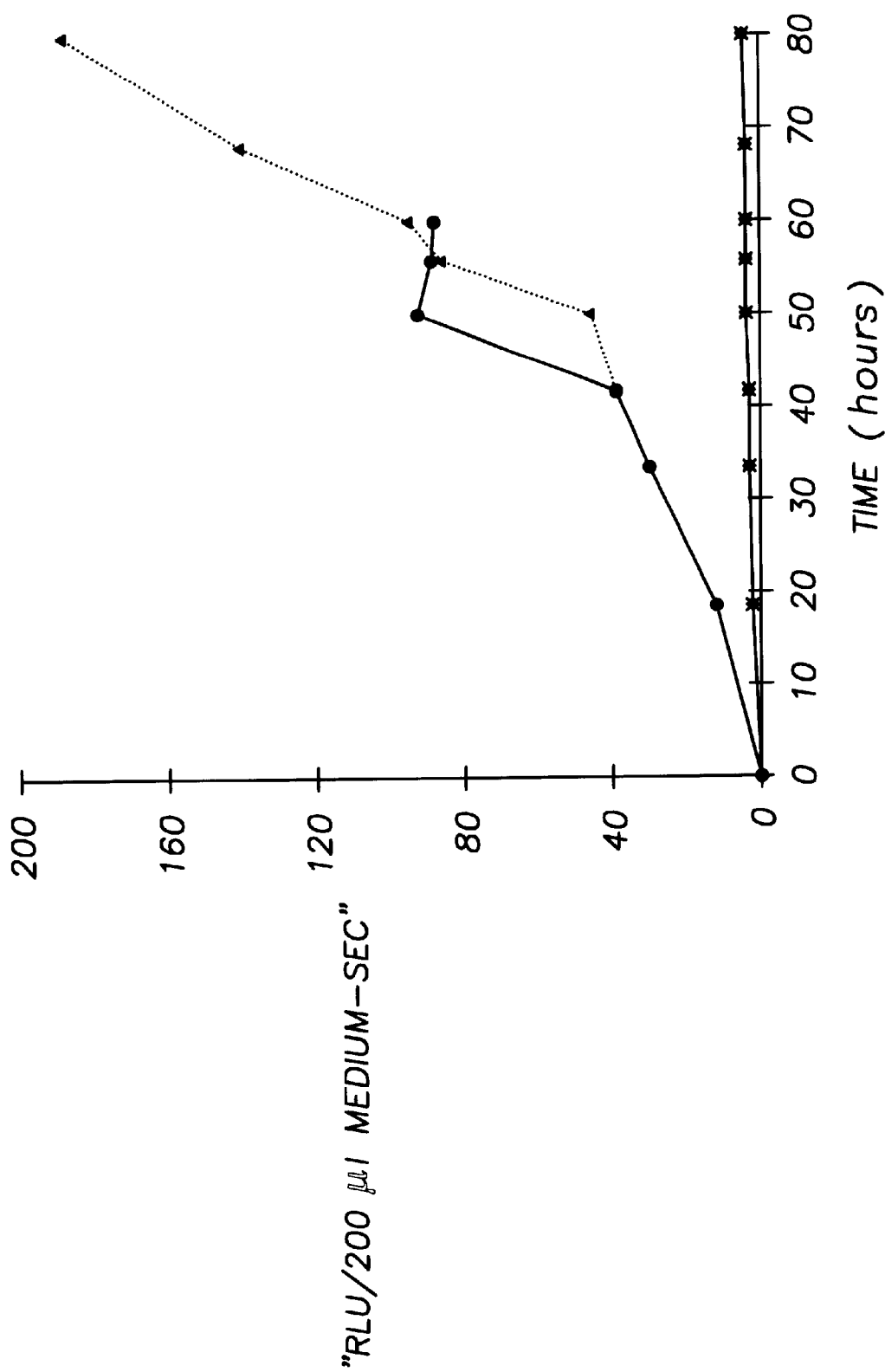
FIG. 6 shows a graph of the time course appearance of Renilla luciferase activity in cell culture media of mammalian cells transfected with pLNCX, pLNCX-RUC, or pLNCX-SRUC.

Referring now to FIG. 6, there is shown a graph of the results of the assays of time course of appearance of Renilla luciferase activity in cell culture media of mammalian cells transfected with plasmid pLNCX-SRUC and grown in DMEM medium supplemented with 10% FBS (circles); transfected with plasmid pLNCX-SRUC and grown in DMEM medium supplemented with 10% FBS for the first 42 hours, and then grown in QBSF 51 medium supplemented with 1% FBS (triangles); transfected with plasmid pLNCX-RUC and grown in DMEM medium supplemented with 10% FBS (diamonds); and transfected with vector only and grown in DMEM medium supplemented with 10% FBS (squares). Relative light units (RLU) are shown as per second, per 200 μl medium.

As can be seen, Renilla luciferase activity could be detected in cell culture medium less than 10 hours after cell transfection, but only with cells transfected with plasmid pLNCX-SRUC (circles and triangles). By contrast, medium taken from plates containing cells transfected with plasmid pLNCX-RUC did not show detectable Renilla luciferase activity (diamonds). In the case of cells transfected with pLNCX-SRUC, luciferase activity increased over time until it reached a plateau 48 hours after transfection. Significantly, while the rate of cell growth was reduced by replacing the medium with QBSF 51 medium supplemented with 1% FBS, luciferase activity continued to increase throughout the study period of 80 hours after transfection (triangles). These results indicate that the Renilla luciferase protein was secreted in cells transfected with pLNCX-SRUC because effect occurred even though the difference in media did not greatly affect luciferase stability (FIG. 3).

F. Immunoblot Analysis of the Presence of Renilla Luciferase in Transfected Cells and in Cell Culture Media The presence of Renilla luciferase in both lysates of transfected cell and in cell culture media was investigated using immunoblot analysis after protein fractionation with SDS-PAGE. For immunoblot analysis of intracellular Renilla luciferase, mammalian COS-7 cells from one plate were washed twice with cold PBS 48 hours after transfection, and harvested by scraping into 100 μl 2×gel-loading buffer (100 mM Tris-HCl, 4% SDS, 20% glycerol, 5% 2-mercaptoethanol, 0.01% bromophenol blue). After complete lysis by sonication, samples were boiled for 3 minutes, centrifuged at 10000×g for 10 minutes to pellet debris, and 20 μl of each sample was loaded on a 12% SDS-polyacrylamide gel. Fractionated proteins were then transferred by electroblotting onto a nylon membrane, reacted with a monoclonal antibody raised against Renilla luciferase, and detected using chemiluminescence. Protein amounts were determined by comparison with a 10 ng of isolated Renilla luciferase protein present on the same blot as a control, using a BioImage Whole Band Analyzer (Genomic Solutions Inc., Ann Arbor, Mich. U.S.).

For immunoblot analysis of secreted Renilla luciferase, 3 ml aliquots of cell culture media (QBSF 51 supplemented with 1% FBS) were taken 48 hours after transfection of COS-7 cells and centrifuged at 10,000×g to pellet cell debris. The aliquots were concentrated down to 0.5 ml using a centriprep concentrator (Amicon, Beverly, Mass., U.S.) with a molecular weight cut off of 15,000. Renilla luciferase present in the concentrates was immunoprecipitated using the Protein A Immunoprecipitation Kit ((Boehringer-Mannheim, Mannheim, Germany) and monoclonal antibody raised against Renilla luciferase, and immunoanalyzed after SDS-PAGE using the same monoclonal antibody.

Figure 7:
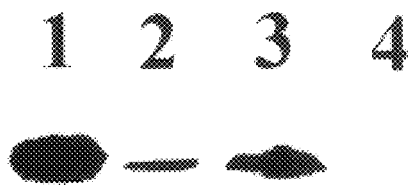
FIG. 7 shows an immunoblot analysis for the presence of Renilla luciferase in total cell lysates for mammalian cells transfected with plasmid pLNCX, pLNCX-SRUC, or pLNCX-SRUC.
Figure 8:
FIG. 8 shows an immunoblot analysis for the presence of Renilla luciferase in cell culture media of mammalian cells that were transfected with plasmid pLNCX, pLNCX-SRUC, or PLNCX-SRUC.

Referring now to FIGS. 7 and 8, there are shown immunoblots of total cell lysates, and of immunoprecipitated cell culture media, respectively, using Renilla luciferase monoclonal antibody. Lane 1 contained 10 ng isolated Renilla luciferase as a control; lane 2 had the mammalian cells that were transfected with plasmid pLNCX-SRUC; lane 3 had the mammalian cells that were transfected with plasmid PLNCX-RUC; and lane 4 had the mammalian cells that were transfected with vector only. Protein amounts were determine by densitometry after comparison with isolated Renilla luciferase protein, lane 1.

Referring now to FIG. 7, protein amounts were calculated to be 0.9 ng for the cells transfected with plasmid pLNCX-SRUC, lane 2, and 1.7 ng for the cells transfected with plasmid pLNCX-RUC, lane 3. The decrease in the amount of luciferase in the cells transfected with plasmid pLNCX-SRUC is an indication that sruc encoded a secreted product which was, therefore, not accumulating in the cytosol. Further, these results indicated that the 15-times increase in luciferase activity measured from lysates of cells expressing the Renilla luciferase gene construct as compared to that measured from lysates of cells expressing the sruc gene construct, FIG. 3, could not be explained by relative amount of Renilla luciferase protein alone.

By contrast, FIG. 8 shows that only the cell culture media of cells transfected with pLNCX-SRUC, lane 2, demonstrated the presence of Renilla luciferase. A protein band of lower molecular weight is also present in lane 2 and faintly in lane 3 and probably represents degradation products of Renilla luciferase.

II. USE OF THE SECRETED FORM OF WILD TYPE RENILLA LUCIFERASE AS A REPORTER PROTEIN

According to one embodiment of the present invention, there is provided a method of using the secreted form of wild type *R. reniformis* luciferase as a reporter protein in a biological assay to study a variety of biological events. The method includes introducing the gene encoding the secreted Renilla luciferase to a cell type or tissue using techniques as will be understood by those with skill with reference to the disclosure herein, such as calcium phosphate co-precipitation, electroporation, lipofection, or naked DNA injection. Samples from the solution surrounding the cells, such as cell culture medium or body fluid, expressing the secreted Renilla luciferase gene are then analyzed. Analysis can include placing the sample solution in an assay buffer, such as 0.5 M NaCl, 1 mM EDTA, and 100 mM potassium phosphate at pH 7.4, and recording light emission for a short period of time (5–10 seconds) after addition of the substrate solution. The method can further include measuring the number of accumulated photons over longer periods of time which increases the sensitivity of the assay because Renilla luciferase catalyzes a "glow-type" of light emission.

The method of using the secreted form of wild type *R. reniformis* luciferase as a reporter protein, according to the present invention, advantageously has a sensitivity in the order of 100 fg, which is three orders of magnitude more sensitive than the assay for secreted human growth hormone. Further advantageously, the method of the present invention is more rapid (less than 1 minute) compared to the secreted AP assay (more than 45 minutes) or to the secreted apoaeqorin assay (more than 2 hours). Also, the method is advantageous as a biological assay in mammals because Renilla luciferase does not have a biological function having an effect on metabolism or development of the animal, such as human growth hormone can have when used in a biological assay.

Additionally advantageously, the method can be used where previously secreted protein can not be removed before the beginning of a time-course study because of the short half-life of Renilla luciferase. For example, secreted Renilla luciferase can be used in a closed system such as monitoring gene expression in animal model systems, including studies of transcriptional activities during animal development, during host-pathogen interactions, or after gene transfer for gene therapy purposes, without killing the animal.

III. PRODUCTION AND EXPRESSION OF POLYPEPTIDE WHICH ENCODES A SECRETED MODIFIED FORM OF WILD TYPE RENILLA LUCIFERASE

A. Construction of Plasmids Encoding the Secreted Wild Type Renilla Luciferase Preprotein Gene and Site-specific Mutagenesis of the Gene Plasmids encoding the secreted wild type Renilla luciferase preprotein gene were constructed and site-specific mutagenesis of the gene using these plasmids were performed as follows. First, the sruc gene, SEQ ID NO:3, encoding the preprotein form of the secreted Renilla luciferase, SEQ ID NO:4, was excised from plasmid pLNCX-SRUC, shown in FIG. 2, as a 1.1 kb HindIII-ClaI DNA fragment with the ClaI site blunt-ended with Klenow enzyme, and was ligated into the HindIII-SmaI sites of plasmid pBluescript KS(+)II (Stratagene, San Diego, Calif., U.S.). The sruc gene, SEQ ID NO:3, was then subcloned as a SalI-XbaI DNA fragment into plasmid vector pND2 (a gift from Gary Rhodes and Robert Malone, unpublished data), under the transcriptional control of the cytomegalovirus promoter, generating plasmid pND2-SRUC, all according to techniques known to those with skill in the art.

Plasmid pND2-SRUC then served as a template for site-directed mutagenesis of the gene, SEQ ID NO:3, encoding the pre-protein form of the secreted Renilla luciferase, SEQ ID NO:4. In summary, the Quick Change Site-Directed Mutagenesis Kit (Stratagene) was used according to the manufacturer's protocol to introduce isolated mutations in SEQ ID NO:3 which caused cysteine to alanine substitutions at positions 52, 101, and 152, and at all three positions 52, 101 and 152, in the pre-protein form of secreted Renilla luciferase, SEQ ID NO:4; where the mutated genes, sruc1, SEQ ID NO:9, coded for SRUC1, SEQ ID NO:10, having a cysteine to alanine substitution at position 52; sruc2, SEQ ID NO:11, coded for SRUC2, SEQ ID NO:12, having a cysteine to alanine substitution at position 101; sruc3, SEQ ID NO:13, coded for SRUC3, SEQ ID NO:14, having a cysteine to alanine substitution at position 152; and sruc4, SEQ ID NO:15, coded for SRUC4, SEQ ID NO:16, having cysteine to alanine substitutions at position 52, 101 and 152; respectively, generating plasmids pND2-SRUC1, pND2-SRUC2, pND2-SRUC3 and pND2-SRUC4, respectively. No substitution was made for the cysteine residue present in the IL-2 leader sequence.

Figure 9:
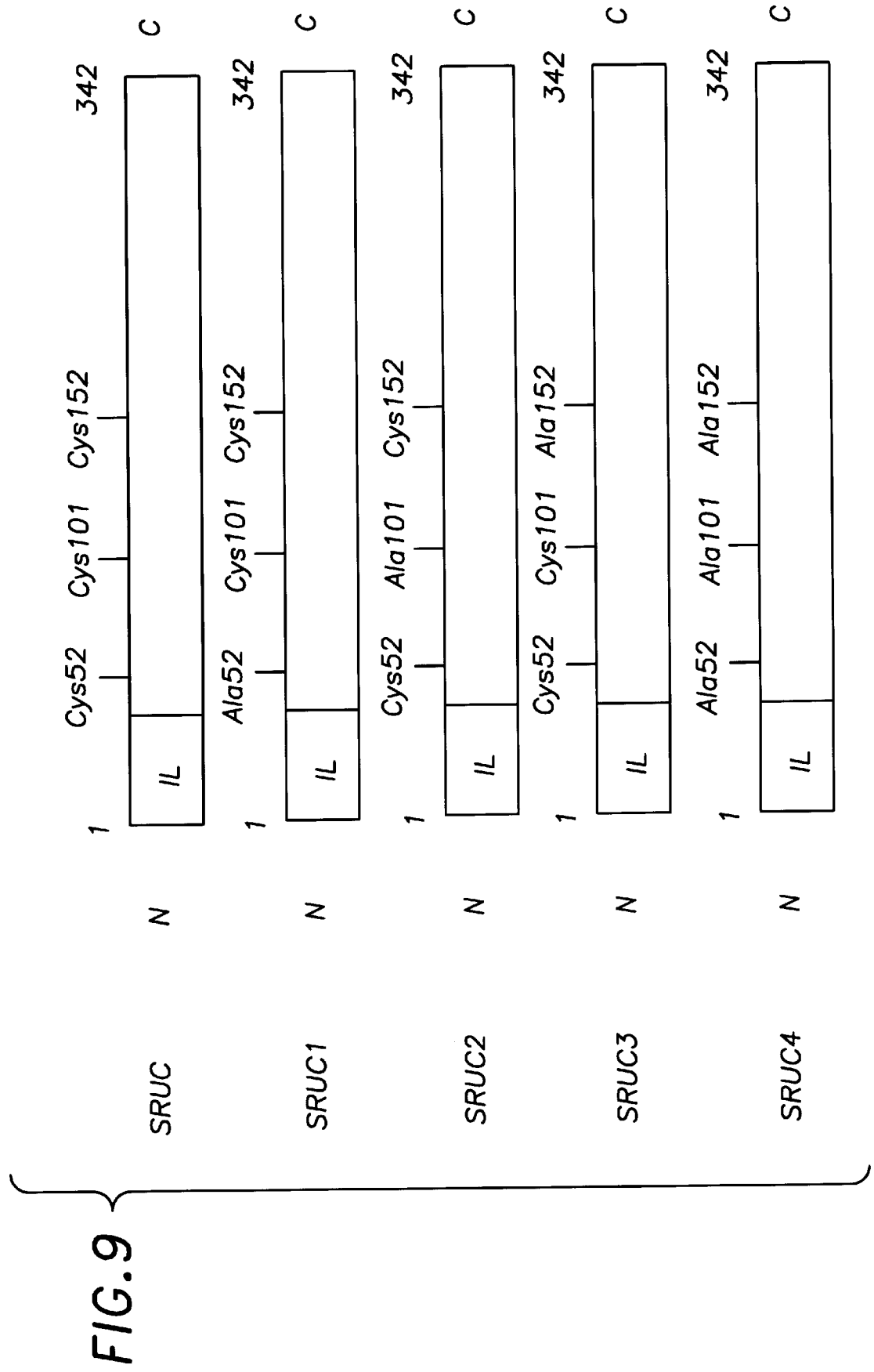
FIG. 9 shows a schematic diagrams of the amino acid sequences of the secreted Renilla luciferase preproteins, SRUC, SRUC1, SRUC2, SRUC3 and SRUC4.

Referring now to FIG. 9, there are shown schematic diagrams of the amino acid sequences of the secreted Renilla luciferases pre-proteins, SRUC1, SEQ ID NO:10; SRUC2, SEQ ID NO:12; SRUC3, SEQ ID NO:14; and SRUC4, SEQ ID NO:16, generated using these techniques, compared with SRUC, SEQ ID NO:4. As can be seen, each sequence was 342 amino acid residues in length and was a fusion of the twenty-three amino acid residues of the human interleukin-2 leader peptide, the five amino acid linker Glu Phe Ser Leu and Lys, and Met, and the 311 amino acid residues of wild type Renilla luciferase pre-protein sequence, SEQ ID NO:2. The first sequence, SRUC, SEQ ID NO:4, contained the complete native Renilla luciferase pre-protein sequence. The second sequence, SRUC1, SEQ ID NO:10, contained a single cysteine to alanine substitution at position 52. The third sequence, SRUC2, SEQ ID NO:12; contained a single cysteine to alanine substitution at position 101. The fourth sequence, SRUC3, SEQ ID NO:14; contained a single cysteine to alanine substitution at position 152. The fifth sequence, SRUC4, SEQ ID NO:16; contained three cysteine to alanine substitutions at positions 52, 101 and 152, SEQ ID NO:4.

B. Transfection of Cultured Mammalian Cells with Plasmids Encoding the Secreted Wild Type Renilla Luciferase Preprotein Gene and Modified Forms of the Secreted Wild Type Renilla Luciferase Preprotein Gene Simian COS-7 cells were cultured and transfected with the plasmids pND2-SRUC1, pND2-SRUC2, pND2-SRUC3 and pND2-SRUC4 as follows. First, some of the mammalian cells were grown in 100 mm tissue culture plates containing 10 ml DMEM medium (Sigma) supplemented with 10% fetal bovine serum (Biowhittaker), and others were grown in Cellgro complete serum free medium (Mediatech, Herndon, Va., U.S.) and 1% fetal bovine serum. Each plate of the cultured mammalian cells were transfected with the 30 $\mu$g of plasmid which comprised 28 $\mu$g of one of the plasmids encoding a secreted Renilla luciferase preprotein gene for experimental purpose and 2 $\mu$g of firefly luciferase plasmid for normalization between experiments using the ProFection Calcium Phosphate System (Promega), according to the manufacturer's instructions. Fifteen hours after transfection, the cells were then washed twice with phosphate-buffered saline. Then, 10 ml of DMEM medium supplemented with 10% FBS was added to the cells grown in this medium and Cellgro complete serum free medium supplemented with 1% FBS was added to the cells grown in this medium.

C. Immiunoblot Analysis of the Presence of Secreted Renilla Luciferase and Modified Forms of the Secreted Renilla Luciferase in Transfected Cells An immunoblot analysis of the secreted Renilla luciferase preprotein and the modified forms of the secreted Renilla luciferase preprotein in lysates of transfected mammalian cells was performed as previously described to determine if the modified secreted Renilla luciferase preproteins retained their full length intracellularly as compared to wild type Renilla luciferase. Briefly, 25 ug of total cell lysates were fractionated using SDS-PAGE, transferred to a membrane, and reacted with rabbit polyclonal antibodies raised against wild-type Renilla luciferase. Referring now to FIG. 10, there is shown an immunoblot analysis for the presence of Renilla luciferase in total cell lysates of mammalian cells transfected with expressing genes encoding SRUC (lane 1), SRUC1 (lane 2), SRUC2 (lane 3), SRUC3 (lane 4), and SRUC4 (lane 5), and isolated from *Escherichia coli* expressing the Renilla luciferase cDNA as control (lane 6). As can be seen, lysates of all of the mammalian cells demonstrate expression of a polypeptide having a weight of about 35.5 kDa, indicating that all of the modified secreted Renilla luciferase preproteins retained their full length.

D. Bioluminescence Assays of Luciferase Activity in Culture Media Containing Secreted Renilla Luciferases and in Cell Lysates of Transfected Mammalian Cells Bioluminescence assays of luciferase activity were performed on cell lysates of mammalian cells transfected with plasmids pND2-SRUC, pND2-SRUC1, pND2-SRUC2, pND2-SRUC3 and pND2-SRUC4; and on culture media (serum free medium supplemented with 1% FBS) containing secreted Renilla luciferases from mammalian cells transfected with plasmids pND2-SRUC, pND2-SRUC 1, pND2-SRUC2, pND2-SRUC3, and pND2-SRUC4 using a Turner TD-20e luminometer 48 hours after transfection. 200 $\mu$l aliquots of cell culture media containing transfected cells with plasmids pND2-SRUC, pND2-SRUC1, pND2-SRUC2, and pND2-SRUC4 were used for each assay. In order to keep the light emission readings within the scale of the luminometer, however, only 2 $\mu$l aliquots of cell culture media containing transfected cells with plasmids pND2-SRUC3 diluted into 198 $\mu$l of culture medium were used for the assay of SRUC3 activity, and then the number of relative light units (RLU) obtained was multiplied by 100. Unmodified coelenterazine was used as a substrate (catalog # C-2944, Molecular Probes).

Referring now to FIG. 11, there is shown a bar graph depicting the results of the measured Renilla luciferase bioluminescence activity in mammalian cell lysates for cells transfected with sruc1 (lane 1), sruc2 (lane 2), sruc3 (lane3), sruc4 (lane 4) and sruc (lane 5As can be seen, mammalian cells transfected with sruc1 demonstrated about half of the Renilla luciferase activity as mammalian cells transfected with sruc. By contrast, mammalian cells transfected with sruc3 demonstrated about three times the Renilla luciferase activity as mammalian cells transfected with sruc. Mammalian cells transfected with either sruc2 or sruc4 did not demonstrate significant intracellular bioluminescence activities.

Referring now to FIG. 12, there is shown a bar graph depicting the results of the measured Renilla luciferase bioluminescence activity in culture media of the same cells transfected with SRUC1 (lane 1), SRUC2 (lane 2), SRUC3 (lane3), SRUC4 (lane 4) and SRUC (lane 5). As can be seen, the culture media of mammalian cells transfected with SRUC3 exhibited a bioluminescence activity of approximately 100 times the culture media of mammalian cells transfected with SRUC. The culture media of mammalian cells transfected with either SRUC1, SRUC2 or SRUC4 did not show significant bioluminescence activity.

Further, the time course of appearance of Renilla luciferase activity was assayed at regular time intervals in cell culture media (Cellgro complete serum free medium supplemented with 1% FBS) containing secreted Renilla luciferases from mammalian cells transfected with plasmids pND2-SRUC, pND2-SRUC1, pND2-SRUC2, pND2-SRUC3, and pND2-SRUC4 over 90 hours after transfection. Referring now to FIG. 13, there is show a graph of the results of the assays of time course of appearance of Renilla luciferase activity in cell culture media. As can be seen, culture media containing secreted Renilla luciferases from mammalian cells transfected with plasmids pND2-SRUC (closed circles) increased for up to about 30 hours after transfection and then decreased steadily towards baseline. By contrast, culture media containing secreted Renilla luciferases from mammalian cells transfected with plasmids pND2-SRUC3 (closed triangles) peaked at about 30 hours but remained relatively high through the end of the assay period. Culture media containing secreted Renilla luciferases from mammalian cells transfected with plasmids pND2-SRUC1 (x's) and pND2-SRUC2 (closed squares) did not show significant activity during the entire 90 hour assay period.

E. Determination of Cell Culture Medium Dependency of Secreted Renilla Luciferase Activity:

Next, a determination was made on whether SRUC3 luciferase activity was dependent on the type of culture medium in which cells secreting that protein were growing as follow. One group of COS-7 cells were transfected with plasmid pND2-SRUC3 grown in DMEM medium supplemented with 10% FBS for 48 hours, and a second group of COS-7 cells were transfected with plasmid pND2-SRUC3 grown in serum free medium supplemented with 1% FBS for 48 hour. Renilla luciferase activity was measured in both cell lysates and culture media.

Referring now to FIG. 14, there are shown bar graphs of the Renilla luciferase activity for cell lysates (cross hatching up to the right) and culture medium (cross hatching up to the left) of cells grown in DMEM supplemented with 10% FBS (left most bars) and cells grown serum free medium (SFM) supplemented with 1% FBS (right most bars). As can be seen, lysates and culture medium of cells grown in DMEM supplemented with 10% FBS showed a two fold and a more than five fold reduction in light emission, respectively, when compared to lysates and culture medium of cells grown serum free medium supplemented with 1% FBS.

F. Measurement of Secreted Renilla Luciferase Stability in Cell Culture Media

In order to determine whether the observed increased bioluminescence activity of SRUC3 compared with SRUC when secreted by mammalian cells, above, was due to increased stability of the SRUC3 luciferase compared with SRUC, the activities of already secreted SRUC and SRUC3 luciferases were measured over time at 37° C. in serum free medium supplemented with 1% FBS. Referring now to FIG. 15, there is shown a graph of the results where the closed diamonds represent bioluminescence activity of SRUC secreted by mammalian cells, and the closed squares represent bioluminescence activity of SRUC secreted by mammalian cells. From the data obtained, the half-life of SRUC and SRUC3 was calculated to be 14 hours and 82 hours, respectively. These stability measurements confirmed that the observed increased bioluminescence activity of SRUC3 compared with SRUC when secreted by mammalian cells, above, was at least in part due to increased stability of the SRUC3 luciferase compared with SRUC.

IV. USE OF SRUC3 AND SEAP GENES IN DUAL REPORTER SYSTEM

A. Construction of Plasmids Encoding sruc3 and seap Genes

First, a plasmid containing the sruc3 gene was reconstructed into retroviral vector pLNCX by cloning a BglII-xbaI DNA fragment from plasmid pND2-SRUC3 into plasmid pLNCX-SRUC, generating plasmid pLNCX-SRUC3. The seap gene, SEQ ID NO:17 (Clontech, Palo Alto, Calif., U.S.), which encodes SEAP protein, SEQ ID NO:18, was cloned into pLNCX (Miller, et al., "Improved retroviral vectors for gene transfer and expression." *Biotechniques* October; 7(9):980–2, 984–6, 989–90 (1989)) as a HindIII-BglI DNA fragment, generating plasmid pLNCX-SEAP, both according to techniques known to those with skill in the art. Both genes were under transcriptional control of the cytomegalovirus promoter.

B. Co-Transfection of Cultured Mammalian Cells with Plasmids pLNCX-SRUC3 and pLNCX-SEAP Simnan COS-7 were grown in DMEM medium supplemented with 10% fetal bovine serum and three culture dishes of cells were transiently co-transfected with plasmids pLNCX-SRUC3 and pLNCX-SEAP using the ProFection Calcium Phosphate System (Promega) according to the manufacturer's instructions in the following ratios: 5 μg sruc3+15 μg seap (dish 1); 10 μg sruc3+10 μg seap (dish 2); and 15 μg sruc3+5 μseap (dish 3)

C. Bioluminescence Assays of Luciferase Activity and Chemiluminescent Assays of Alkaline Phosphatase Activity in Culture Media Containing Secreted Renilla Luciferase and Secreted Alkaline Phosphatase The Renilla luciferase activity assay was performed as described above, and the alkaline phosphatase assay was performed according to the manufacturer's protocol (Clontech) 48 hours after co-transfection from centrifuged cell culture media. Light emission was measured in relative light units (RLU) using a Turner TD-20e luminometer. The Renilla luciferase and alkaline phosphatase assays were done with 50 μl and 1 μl of media, respectively, and SEAP measurements were multiplied by a correction factor of 50.

Referring now to FIGS. 16 and 17, there are shown bar graphs of the results of the bioluminescence assays of luciferase activity, and the chemiluminescent assays of alkaline phosphatase activity, respectively. As can be seen, the sruc3 and seap genes were co-expressed in mammalian cells, indicating that these genes can be used in a dual reporter assay system. This dual reporter assay system based on secreted Renilla luciferase and an additional secreted light emitting protein is simple to perform, since no cell harvesting and lysis are involved. Other genes encoding light secreting proteins which can be used with secreted Renilla luciferase include secreted alkaline phosphatase, and Vargula luciferase. Further, the light emission catalyzed by SRUC3 increased proportionally with increased amounts of DNA, indicating that sensitivity of the SRUC3 assay could be increased relative to the other light emitting protein assay in mammalian cells.

V. CONSTRUCTION OF STABLE MAMMALIAN PACKAGING CELL LINES WHICH PRODUCE RETROVIRUSES CARRYING THE SRUC3 GENE

A stable mammalian packaging cell lines which produced retroviruses carrying the sruc3 gene was produced as follows. First, ecotropic GP+E86 retroviral packaging cells were transfected with 20 μg of plasmid pLNCX-SRUC3 using the ProFection Calcium Phosphate System (Promega) according to the manufacturer's instructions. Then, supernatants obtained from stable GP+E86 cell lines transfected with pLNCX-SRUC3 were used for transduction of amphotropic packaging cell line PA317. Sixty-one stable transformants were obtained after selection in presence of G418 and Renilla luciferase activity was measured in their culture media.

Referring now to FIG. 18, there is shown a chart of the range of Renilla luciferase activities measured in 100 μl aliquots of media of 61 stable PA317 packaging cell lines transduced with retroviruses carrying the sruc3 gene. As can be seen, 85% of the isolated PA3 17 colonies demonstrated some level of Renilla luciferase activity in their culture media and 8% of the isolated PA317 colonies showed high levels of Renilla luciferase activity in their culture media (greater than 1000 RLU). These results indicate that the sruc3 gene can be stably expressed at high levels in mammalian cells.

All documents cited herein are incorporated herein by reference in their entirety.

Although the present invention has been discussed in considerable detail with reference to certain preferred embodiments, other embodiments are possible. Therefore, the spirit and scope of the appended claims should not be limited to the description of preferred embodiments contained herein.

We claim:

1. A polynucleotide encoding an amino acid sequence according to SEQ ID NO:14.

2. A method of performing a biological assay comprising:
   a) providing a host cell transfected with the polynucleotide of claim 1; and
   b) growing the host cell in a culture medium, and where the method additionally comprises detecting light emission from the Renilla luciferase coded by the polynucleotide that has been secreted in the culture medium.

3. The method of performing a biological assay of claim 2, where the host cell is a mammalian cell.

4. The method of performing a biological assay of claim 2, additionally comprising transfecting the host cell with a second polynucleotide encoding a second light emitting protein.

5. The method of performing a biological assay of claim 4, where the second light emitting protein coded by the second polynucleotide is seap.

6. The method of performing a biological assay of claim 4, where the method additionally comprises detecting light emission from the second light emitting protein coded by the second polynucleotide that has been secreted in the culture medium.

7. A plasmid containing the polynucleotide of claim 1.

8. A vector containing the polynucleotide of claim 1.

9. A host cell transfected with the polynucleotide of claim 1.

10. A mammalian host cell transfected with the polynucleotide of claim 1.

11. A kit for performing a biological assay, comprising the polynucleotide of claim 1.

12. The kit of claim 11, additionally comprising a second polynucleotide.

13. The kit of claim 12, where the second polynucleotide is seap.

14. A stable mammalian packaging cell line which produces retroviruses carrying a polynucleotide of claim 1.

15. The stable mammalian packaging cell line of claim 14, where the polynucleotide comprises the sequence of SEQ ID NO:13.

* * * * *

SEQUENCE LISTING

<160> NUMBER OF SEQ ID NOS: 18

<210> SEQ ID NO 1
<211> LENGTH: 1196
<212> TYPE: DNA
<213> ORGANISM: Renilla reniformis
<220> FEATURE:
<221> NAME/KEY: CDS
<222> LOCATION: (10)..(945)

<400> SEQUENCE: 1

```
agcttaaag atg act tcg aaa gtt tat gat cca gaa caa agg aaa cgg atg      51
         Met Thr Ser Lys Val Tyr Asp Pro Glu Gln Arg Lys Arg Met
           1               5                  10 ata act ggt ccg cag tgg tgg gcc aga tgt aaa caa atg aat gtt ctt       99
Ile Thr Gly Pro Gln Trp Trp Ala Arg Cys Lys Gln Met Asn Val Leu
 15                  20                  25                  30
```

-continued

| | | |
|---|---|---|
| gat tca ttt att aat tat tat gat tca gaa aaa cat gca gaa aat gct<br>Asp Ser Phe Ile Asn Tyr Tyr Asp Ser Glu Lys His Ala Glu Asn Ala<br>35                    40                  45 | 147 |
| gtt att ttt tta cat ggt aac gcg gcc tct tct tat tta tgg cga cat<br>Val Ile Phe Leu His Gly Asn Ala Ala Ser Ser Tyr Leu Trp Arg His<br>50                    55                60 | 195 |
| gtt gtg cca cat att gag cca gta gcg cgg tgt att ata cca gat ctt<br>Val Val Pro His Ile Glu Pro Val Ala Arg Cys Ile Ile Pro Asp Leu<br>      65                  70                75 | 243 |
| att ggt atg ggc aaa tca ggc aaa tct ggt aat ggt tct tat agg tta<br>Ile Gly Met Gly Lys Ser Gly Lys Ser Gly Asn Gly Ser Tyr Arg Leu<br>80                    85                90 | 291 |
| ctt gat cat tac aaa tat ctt act gca tgg ttt gaa ctt ctt aat tta<br>Leu Asp His Tyr Lys Tyr Leu Thr Ala Trp Phe Glu Leu Leu Asn Leu<br>95                    100              105              110 | 339 |
| cca aag aag atc att ttt gtc ggc cat gat tgg ggt gct tgt ttg gca<br>Pro Lys Lys Ile Ile Phe Val Gly His Asp Trp Gly Ala Cys Leu Ala<br>                  115              120              125 | 387 |
| ttt cat tat agc tat gag cat caa gat aag atc aaa gca ata gtt cac<br>Phe His Tyr Ser Tyr Glu His Gln Asp Lys Ile Lys Ala Ile Val His<br>130                  135              140 | 435 |
| gct gaa agt gta gta gat gtg att gaa tca tgg gat gaa tgg cct gat<br>Ala Glu Ser Val Val Asp Val Ile Glu Ser Trp Asp Glu Trp Pro Asp<br>145                  150              155 | 483 |
| att gaa gaa gat att gcg ttg atc aaa tct gaa gaa gga gaa aaa atg<br>Ile Glu Glu Asp Ile Ala Leu Ile Lys Ser Glu Glu Gly Glu Lys Met<br>160                  165              170 | 531 |
| gtt ttg gag aat aac ttc ttc gtg gaa acc atg ttg cca tca aaa atc<br>Val Leu Glu Asn Asn Phe Phe Val Glu Thr Met Leu Pro Ser Lys Ile<br>175                  180              185              190 | 579 |
| atg aga aag tta gaa cca gaa gaa ttt gca gca tat ctt gaa cca ttc<br>Met Arg Lys Leu Glu Pro Glu Glu Phe Ala Ala Tyr Leu Glu Pro Phe<br>                  195              200              205 | 627 |
| aaa gag aaa ggt gaa gtt cgt cgt cca aca tta tca tgg cct cgt gaa<br>Lys Glu Lys Gly Glu Val Arg Arg Pro Thr Leu Ser Trp Pro Arg Glu<br>210                  215              220 | 675 |
| atc ccg tta gta aaa ggt ggt aaa cct gac gtt gta caa att gtt agg<br>Ile Pro Leu Val Lys Gly Gly Lys Pro Asp Val Val Gln Ile Val Arg<br>225                  230              235 | 723 |
| aat tat aat gct tat cta cgt gca agt gat gat tta cca aaa atg ttt<br>Asn Tyr Asn Ala Tyr Leu Arg Ala Ser Asp Asp Leu Pro Lys Met Phe<br>240                  245              250 | 771 |
| att gaa tcg gat cca gga ttc ttt tcc aat gct att gtt gaa ggc gcc<br>Ile Glu Ser Asp Pro Gly Phe Phe Ser Asn Ala Ile Val Glu Gly Ala<br>255                  260              265              270 | 819 |
| aag aag ttt cct aat act gaa ttt gtc aaa gta aaa ggt ctt cat ttt<br>Lys Lys Phe Pro Asn Thr Glu Phe Val Lys Val Lys Gly Leu His Phe<br>                  275              280              285 | 867 |
| tcg caa gaa gat gca cct gat gaa atg gga aaa tat atc aaa tcg ttc<br>Ser Gln Glu Asp Ala Pro Asp Glu Met Gly Lys Tyr Ile Lys Ser Phe<br>290                  295              300 | 915 |
| gtt gag cga gtt ctc aaa aat gaa caa taa ttactttggt tttttattta<br>Val Glu Arg Val Leu Lys Asn Glu Gln<br>305                  310 | 965 |
| cattttccc gggtttaata atataaatgt cattttcaac aattttattt taactgaata | 1025 |
| tttcacaggg aacattcata tatgttgatt aatttagctc gaactttact ctgtcatatc | 1085 |
| attttggaat attacctctt tcaatgaaac tttataaaca gtggttcaat taattaatat | 1145 | atattataat tacatttgtt atgtaataaa ctcggtttta ttataaaaaa a    1196

<210> SEQ ID NO 2
<211> LENGTH: 311
<212> TYPE: PRT
<213> ORGANISM: Renilla reniformis

<400> SEQUENCE: 2

```
Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```

<210> SEQ ID NO 3
<211> LENGTH: 1271
<212> TYPE: DNA
<213> ORGANISM: Renilla reniformis
<220> FEATURE:
<221> NAME/KEY: CDS
<222> LOCATION: (1)..(1017)

-continued

```
<400> SEQUENCE: 3 atg tac agg atg caa ctc ctg tct tgc att gca cta agt ctt gca ctt      48
Met Tyr Arg Met Gln Leu Leu Ser Cys Ile Ala Leu Ser Leu Ala Leu
 1               5                  10                  15 gtc aca aac agt gca cct act gaa ttc agc tta aag atg act tcg aaa      96
Val Thr Asn Ser Ala Pro Thr Glu Phe Ser Leu Lys Met Thr Ser Lys
                20                  25                  30 gtt tat gat cca gaa caa agg aaa cgg atg ata act ggt ccg cag tgg     144
Val Tyr Asp Pro Glu Gln Arg Lys Arg Met Ile Thr Gly Pro Gln Trp
            35                  40                  45 tgg gcc aga tgt aaa caa atg aat gtt ctt gat tca ttt att aat tat     192
Trp Ala Arg Cys Lys Gln Met Asn Val Leu Asp Ser Phe Ile Asn Tyr
        50                  55                  60 tat gat tca gaa aaa cat gca gaa aat gct gtt att ttt tta cat ggt     240
Tyr Asp Ser Glu Lys His Ala Glu Asn Ala Val Ile Phe Leu His Gly
 65                  70                  75                  80 aac gcg gcc tct tct tat tta tgg cga cat gtt gtg cca cat att gag     288
Asn Ala Ala Ser Ser Tyr Leu Trp Arg His Val Val Pro His Ile Glu
                 85                  90                  95 cca gta gcg cgg tgt att ata cca gat ctt att ggt atg ggc aaa tca     336
Pro Val Ala Arg Cys Ile Ile Pro Asp Leu Ile Gly Met Gly Lys Ser
            100                 105                 110 ggc aaa tct ggt aat ggt tct tat agg tta ctt gat cat tac aaa tat     384
Gly Lys Ser Gly Asn Gly Ser Tyr Arg Leu Leu Asp His Tyr Lys Tyr
        115                 120                 125 ctt act gca tgg ttt gaa ctt ctt aat tta cca aag aag atc att ttt     432
Leu Thr Ala Trp Phe Glu Leu Leu Asn Leu Pro Lys Lys Ile Ile Phe
    130                 135                 140 gtc ggc cat gat tgg ggt gct tgt ttg gca ttt cat tat agc tat gag     480
Val Gly His Asp Trp Gly Ala Cys Leu Ala Phe His Tyr Ser Tyr Glu
145                 150                 155                 160 cat caa gat aag atc aaa gca ata gtt cac gct gaa agt gta gta gat     528
His Gln Asp Lys Ile Lys Ala Ile Val His Ala Glu Ser Val Val Asp
                165                 170                 175 gtg att gaa tca tgg gat gaa tgg cct gat att gaa gaa gat att gcg     576
Val Ile Glu Ser Trp Asp Glu Trp Pro Asp Ile Glu Glu Asp Ile Ala
            180                 185                 190 ttg atc aaa tct gaa gaa gga gaa aaa atg gtt ttg gag aat aac ttc     624
Leu Ile Lys Ser Glu Glu Gly Glu Lys Met Val Leu Glu Asn Asn Phe
        195                 200                 205 ttc gtg gaa acc atg ttg cca tca aaa atc atg aga aag tta gaa cca     672
Phe Val Glu Thr Met Leu Pro Ser Lys Ile Met Arg Lys Leu Glu Pro
    210                 215                 220 gaa gaa ttt gca gca tat ctt gaa cca ttc aaa gag aaa ggt gaa gtt     720
Glu Glu Phe Ala Ala Tyr Leu Glu Pro Phe Lys Glu Lys Gly Glu Val
225                 230                 235                 240 cgt cgt cca aca tta tca tgg cct cgt gaa atc ccg tta gta aaa ggt     768
Arg Arg Pro Thr Leu Ser Trp Pro Arg Glu Ile Pro Leu Val Lys Gly
                245                 250                 255 ggt aaa cct gac gtt gta caa att gtt agg aat tat aat gct tat cta     816
Gly Lys Pro Asp Val Val Gln Ile Val Arg Asn Tyr Asn Ala Tyr Leu
            260                 265                 270 cgt gca agt gat gat tta cca aaa atg ttt att gaa tcg gat cca gga     864
Arg Ala Ser Asp Asp Leu Pro Lys Met Phe Ile Glu Ser Asp Pro Gly
        275                 280                 285 ttc ttt tcc aat gct att gtt gaa ggc gcc aag aag ttt cct aat act     912
Phe Phe Ser Asn Ala Ile Val Glu Gly Ala Lys Lys Phe Pro Asn Thr
    290                 295                 300 gaa ttt gtc aaa gta aaa ggt ctt cat ttt tcg caa gaa gat gca cct     960
```

```
Glu Phe Val Lys Val Lys Gly Leu His Phe Ser Gln Glu Asp Ala Pro
305                 310                 315                 320 gat gaa atg gga aaa tat atc aaa tcg ttc gtt gag cga gtt ctc aaa    1008
Asp Glu Met Gly Lys Tyr Ile Lys Ser Phe Val Glu Arg Val Leu Lys
                325                 330                 335 aat gaa caa taattacttt ggtttttat ttacatttttt cccgggttta            1057
Asn Glu Gln ataatataaa tgtcattttc aacaatttta ttttaactga atatttcaca gggaacattc  1117
atatatgttg attaatttag ctcgaacttt actctgtcat atcattttgg aatattacct  1177
ctttcaatga aactttataa acagtggttc aattaattaa tatatattat aattacattt  1237
gttatgtaat aaactcggtt ttattataaa aaaa                              1271

<210> SEQ ID NO 4
<211> LENGTH: 339
<212> TYPE: PRT
<213> ORGANISM: Renilla reniformis

<400> SEQUENCE: 4

Met Tyr Arg Met Gln Leu Leu Ser Cys Ile Ala Leu Ser Leu Ala Leu
1               5                   10                  15

Val Thr Asn Ser Ala Pro Thr Glu Phe Ser Leu Lys Met Thr Ser Lys
                20                  25                  30

Val Tyr Asp Pro Glu Gln Arg Lys Arg Met Ile Thr Gly Pro Gln Trp
            35                  40                  45

Trp Ala Arg Cys Lys Gln Met Asn Val Leu Asp Ser Phe Ile Asn Tyr
        50                  55                  60

Tyr Asp Ser Glu Lys His Ala Glu Asn Ala Val Ile Phe Leu His Gly
65                  70                  75                  80

Asn Ala Ala Ser Ser Tyr Leu Trp Arg His Val Val Pro His Ile Glu
                85                  90                  95

Pro Val Ala Arg Cys Ile Ile Pro Asp Leu Ile Gly Met Gly Lys Ser
            100                 105                 110

Gly Lys Ser Gly Asn Gly Ser Tyr Arg Leu Leu Asp His Tyr Lys Tyr
        115                 120                 125

Leu Thr Ala Trp Phe Glu Leu Leu Asn Leu Pro Lys Lys Ile Ile Phe
130                 135                 140

Val Gly His Asp Trp Gly Ala Cys Leu Ala Phe His Tyr Ser Tyr Glu
145                 150                 155                 160

His Gln Asp Lys Ile Lys Ala Ile Val His Ala Glu Ser Val Val Asp
                165                 170                 175

Val Ile Glu Ser Trp Asp Glu Trp Pro Asp Ile Glu Glu Asp Ile Ala
            180                 185                 190

Leu Ile Lys Ser Glu Glu Gly Glu Lys Met Val Leu Glu Asn Asn Phe
        195                 200                 205

Phe Val Glu Thr Met Leu Pro Ser Lys Ile Met Arg Lys Leu Glu Pro
210                 215                 220

Glu Glu Phe Ala Ala Tyr Leu Glu Pro Phe Lys Glu Lys Gly Glu Val
225                 230                 235                 240

Arg Arg Pro Thr Leu Ser Trp Pro Arg Glu Ile Pro Leu Val Lys Gly
                245                 250                 255

Gly Lys Pro Asp Val Val Gln Ile Val Arg Asn Tyr Asn Ala Tyr Leu
            260                 265                 270

Arg Ala Ser Asp Asp Leu Pro Lys Met Phe Ile Glu Ser Asp Pro Gly
        275                 280                 285
```

```
Phe Phe Ser Asn Ala Ile Val Glu Gly Ala Lys Lys Phe Pro Asn Thr
    290                 295                 300

Glu Phe Val Lys Val Lys Gly Leu His Phe Ser Gln Glu Asp Ala Pro
305                 310                 315                 320

Asp Glu Met Gly Lys Tyr Ile Lys Ser Phe Val Glu Arg Val Leu Lys
                325                 330                 335

Asn Glu Gln

<210> SEQ ID NO 5
<211> LENGTH: 87
<212> TYPE: DNA
<213> ORGANISM: Artificial Sequence
<220> FEATURE:
<223> OTHER INFORMATION: DNA encoding the 23 amino acid residue signal
      sequence of human I L-2 protein (IL2SP), GenBank accession number
      AJ00264, followed by a 5 amino acid linker and by the methionine
      start codon of wild type Renilla luciferase, ATG

<400> SEQUENCE: 5
atgtacagga tgcaactcct gtcttgcatt gcactaagtc ttgcacttgt cacaaacagt      60
gcacctactg aattcagctt aaagatg                                          87

<210> SEQ ID NO 6
<211> LENGTH: 29
<212> TYPE: DNA
<213> ORGANISM: Artificial Sequence
<220> FEATURE:
<223> OTHER INFORMATION: PCR primer

<400> SEQUENCE: 6
tttgaattca tgtacaggat gcaactcct                                        29

<210> SEQ ID NO 7
<211> LENGTH: 29
<212> TYPE: DNA
<213> ORGANISM: Artificial Sequence
<220> FEATURE:
<223> OTHER INFORMATION: PCR primer

<400> SEQUENCE: 7
tttgaattca gtagtgcact gtttgtgac                                        29

<210> SEQ ID NO 8
<211> LENGTH: 30
<212> TYPE: DNA
<213> ORGANISM: Artificial Sequence
<220> FEATURE:
<223> OTHER INFORMATION: PCR primer

<400> SEQUENCE: 8
tttcccggga aaatgtaaa taaaaaacca                                        30

<210> SEQ ID NO 9
<211> LENGTH: 2542
<212> TYPE: DNA
<213> ORGANISM: Artificial Sequence
<220> FEATURE:
<221> NAME/KEY: CDS
<222> LOCATION: (1)..(1017)
<223> OTHER INFORMATION: DNA encoding pre-protein form of secreted
      Renilla luciferase having a cysteine to alanine substitution at
      position 52

<400> SEQUENCE: 9
```

-continued

| | |
|---|---|
| atg tac agg atg caa ctc ctg tct tgc att gca cta agt ctt gca ctt<br>Met Tyr Arg Met Gln Leu Leu Ser Cys Ile Ala Leu Ser Leu Ala Leu<br>1               5                  10                 15 | 48 |
| gtc aca aac agt gca cct act gaa ttc agc tta aag atg act tcg aaa<br>Val Thr Asn Ser Ala Pro Thr Glu Phe Ser Leu Lys Met Thr Ser Lys<br>        20                  25                 30 | 96 |
| gtt tat gat cca gaa caa agg aaa cgg atg ata act ggt ccg cag tgg<br>Val Tyr Asp Pro Glu Gln Arg Lys Arg Met Ile Thr Gly Pro Gln Trp<br>                35                 40                 45 | 144 |
| tgg gcc aga gct aaa caa atg aat gtt ctt gat tca ttt att aat tat<br>Trp Ala Arg Ala Lys Gln Met Asn Val Leu Asp Ser Phe Ile Asn Tyr<br>     50                 55                 60 | 192 |
| tat gat tca gaa aaa cat gca gaa aat gct gtt att ttt tta cat ggt<br>Tyr Asp Ser Glu Lys His Ala Glu Asn Ala Val Ile Phe Leu His Gly<br>65                 70                 75                 80 | 240 |
| aac gcg gcc tct tct tat tta tgg cga cat gtt gtg cca cat att gag<br>Asn Ala Ala Ser Ser Tyr Leu Trp Arg His Val Val Pro His Ile Glu<br>                   85                 90                 95 | 288 |
| cca gta gcg cgg tgt att ata cca gat ctt att ggt atg ggc aaa tca<br>Pro Val Ala Arg Cys Ile Ile Pro Asp Leu Ile Gly Met Gly Lys Ser<br>             100                105                110 | 336 |
| ggc aaa tct ggt aat ggt tct tat agg tta ctt gat cat tac aaa tat<br>Gly Lys Ser Gly Asn Gly Ser Tyr Arg Leu Leu Asp His Tyr Lys Tyr<br>        115                120                125 | 384 |
| ctt act gca tgg ttt gaa ctt ctt aat tta cca aag aag atc att ttt<br>Leu Thr Ala Trp Phe Glu Leu Leu Asn Leu Pro Lys Lys Ile Ile Phe<br>130                135                140 | 432 |
| gtc ggc cat gat tgg ggt gct tgt ttg gca ttt cat tat agc tat gag<br>Val Gly His Asp Trp Gly Ala Cys Leu Ala Phe His Tyr Ser Tyr Glu<br>145                150                155                160 | 480 |
| cat caa gat aag atc aaa gca ata gtt cac gct gaa agt gta gta gat<br>His Gln Asp Lys Ile Lys Ala Ile Val His Ala Glu Ser Val Val Asp<br>                165                170                175 | 528 |
| gtg att gaa tca tgg gat gaa tgg cct gat att gaa gaa gat att gcg<br>Val Ile Glu Ser Trp Asp Glu Trp Pro Asp Ile Glu Glu Asp Ile Ala<br>           180                185                190 | 576 |
| ttg atc aaa tct gaa gaa gga gaa aaa atg gtt ttg gag aat aac ttc<br>Leu Ile Lys Ser Glu Glu Gly Glu Lys Met Val Leu Glu Asn Asn Phe<br>      195                200                205 | 624 |
| ttc gtg gaa acc atg ttg cca tca aaa atc atg aga aag tta gaa cca<br>Phe Val Glu Thr Met Leu Pro Ser Lys Ile Met Arg Lys Leu Glu Pro<br>210                215                220 | 672 |
| gaa gaa ttt gca gca tat ctt gaa cca ttc aaa gag aaa ggt gaa gtt<br>Glu Glu Phe Ala Ala Tyr Leu Glu Pro Phe Lys Glu Lys Gly Glu Val<br>225                230                235                240 | 720 |
| cgt cgt cca aca tta tca tgg cct cgt gaa atc ccg tta gta aaa ggt<br>Arg Arg Pro Thr Leu Ser Trp Pro Arg Glu Ile Pro Leu Val Lys Gly<br>                245                250                255 | 768 |
| ggt aaa cct gac gtt gta caa att gtt agg aat tat aat gct tat cta<br>Gly Lys Pro Asp Val Val Gln Ile Val Arg Asn Tyr Asn Ala Tyr Leu<br>            260                265                270 | 816 |
| cgt gca agt gat gat tta cca aaa atg ttt att gaa tcg gat cca gga<br>Arg Ala Ser Asp Asp Leu Pro Lys Met Phe Ile Glu Ser Asp Pro Gly<br>       275                280                285 | 864 |
| ttc ttt tcc aat gct att gtt gaa ggc gcc aag aag ttt cct aat act<br>Phe Phe Ser Asn Ala Ile Val Glu Gly Ala Lys Lys Phe Pro Asn Thr<br>290                295                300 | 912 |
| gaa ttt gtc aaa gta aaa ggt ctt cat ttt tcg caa gaa gat gca cct<br>Glu Phe Val Lys Val Lys Gly Leu His Phe Ser Gln Glu Asp Ala Pro<br>305                310                315                320 | 960 |

-continued

```
gat gaa atg gga aaa tat atc aaa tcg ttc gtt gag cga gtt ctc aaa      1008
Asp Glu Met Gly Lys Tyr Ile Lys Ser Phe Val Glu Arg Val Leu Lys
                325                 330                 335 aat gaa caa taattactttt ggttttttat ttacattttt cccgggttta             1057
Asn Glu Gln ataatataaa tgtcattttc aacaatttta ttttaactga atatttcaca gggaacattc    1117
atatatgttg attaatttag ctcgaacttt actctgtcat atcattttgg aatattacct    1177
ctttcaatga aactttataa acagtggttc aattaattaa tatatattat aattacattt    1237
gttatgtaat aaactcggtt ttattataaa aaaaatgtac aggatgcaac tcctgtcttg    1297
cattgcacta agtcttgcac ttgtcacaaa cagtgcacct actgaattca gcttaaagat    1357
gacttcgaaa gtttatgatc agaacaaag gaaacggatg ataactggtc cgcagtggtg     1417
ggccagagct aaacaaatga atgttcttga ttcatttatt aattattatg attcagaaaa    1477
acatgcagaa aatgctgtta ttttttaca tggtaacgcg gcctcttctt atttatggcg     1537
acatgttgtg ccacatattg agccagtagc gcggtgtatt ataccagatc ttattggtat    1597
gggcaaatca ggcaaatctg gtaatggttc ttataggtta cttgatcatt acaaatatct    1657
tactgcatgg tttgaacttc ttaatttacc aaagaagatc attttttgtcg gccatgattg   1717
gggtgcttgt ttggcatttc attatagcta tgagcatcaa gataagatca aagcaatagt    1777
tcacgctgaa agtgtagtag atgtgattga atcatgggat gaatggcctg atattgaaga    1837
agatattgcg ttgatcaaat ctgaagaagg agaaaaaatg gttttggaga ataacttctt    1897
cgtggaaacc atgttgccat caaaaatcat gagaaagtta gaaccagaag aatttgcagc    1957
atatcttgaa ccattcaaag agaaaggtga agttcgtcgt ccaacattat catggcctcg    2017
tgaaatcccg ttagtaaaag gtggtaaacc tgacgttgta caaattgtta ggaattataa    2077
tgcttatcta cgtgcaagtg atgatttacc aaaaatgttt attgaatcgg atccaggatt    2137
cttttccaat gctattgttg aaggcgccaa gaagtttcct aatactgaat tgtcaaagt     2197
aaaaggtctt cattttttcgc aagaagatgc acctgatgaa atgggaaaat atatcaaatc    2257
gttcgttgag cgagttctca aaaatgaaca ataattactt tggttttttta tttacattttt 2317
tcccgggttt aataatataa atgtcatttt caacaatttt attttaactg aatatttcac    2377
agggaacatt catatatgtt gattaattta gctcgaactt tactctgtca tatcattttg    2437
gaatattacc tctttcaatg aaactttata acagtggtt caattaatta atatatatta     2497
taattacatt tgttatgtaa taaactcggt tttattataa aaaaa                    2542
```

<210> SEQ ID NO 10
<211> LENGTH: 339
<212> TYPE: PRT
<213> ORGANISM: Artificial Sequence
<220> FEATURE:
<223> OTHER INFORMATION: pre-protein form of secreted Renilla luciferase
      having a cysteine to alanine substitution at position 52

<400> SEQUENCE: 10

```
Met Tyr Arg Met Gln Leu Leu Ser Cys Ile Ala Leu Ser Leu Ala Leu
1               5                   10                  15

Val Thr Asn Ser Ala Pro Thr Glu Phe Ser Leu Lys Met Thr Ser Lys
                20                  25                  30

Val Tyr Asp Pro Glu Gln Arg Lys Arg Met Ile Thr Gly Pro Gln Trp
            35                  40                  45

Trp Ala Arg Ala Lys Gln Met Asn Val Leu Asp Ser Phe Ile Asn Tyr
```

```
              50                  55                  60
Tyr Asp Ser Lys His Ala Glu Asn Ala Val Ile Phe Leu His Gly
 65                  70                  75                  80

Asn Ala Ser Ser Tyr Leu Trp Arg His Val Pro His Ile Glu
                 85                  90                  95

Pro Val Ala Arg Cys Ile Ile Pro Asp Leu Ile Gly Met Gly Lys Ser
                100                 105                 110

Gly Lys Ser Gly Asn Gly Ser Tyr Arg Leu Leu Asp His Tyr Lys Tyr
            115                 120                 125

Leu Thr Ala Trp Phe Glu Leu Leu Asn Leu Pro Lys Lys Ile Ile Phe
        130                 135                 140

Val Gly His Asp Trp Gly Ala Cys Leu Ala Phe His Tyr Ser Tyr Glu
145                 150                 155                 160

His Gln Asp Lys Ile Lys Ala Ile Val His Ala Glu Ser Val Val Asp
                165                 170                 175

Val Ile Glu Ser Trp Asp Glu Trp Pro Asp Ile Glu Glu Asp Ile Ala
            180                 185                 190

Leu Ile Lys Ser Glu Glu Gly Glu Lys Met Val Leu Glu Asn Asn Phe
        195                 200                 205

Phe Val Glu Thr Met Leu Pro Ser Lys Ile Met Arg Lys Leu Glu Pro
210                 215                 220

Glu Glu Phe Ala Ala Tyr Leu Glu Pro Phe Lys Glu Lys Gly Glu Val
225                 230                 235                 240

Arg Arg Pro Thr Leu Ser Trp Pro Arg Glu Ile Pro Leu Val Lys Gly
                245                 250                 255

Gly Lys Pro Asp Val Val Gln Ile Val Arg Asn Tyr Asn Ala Tyr Leu
            260                 265                 270

Arg Ala Ser Asp Asp Leu Pro Lys Met Phe Ile Glu Ser Asp Pro Gly
        275                 280                 285

Phe Phe Ser Asn Ala Ile Val Glu Gly Ala Lys Lys Phe Pro Asn Thr
290                 295                 300

Glu Phe Val Lys Val Lys Gly Leu His Phe Ser Gln Glu Asp Ala Pro
305                 310                 315                 320

Asp Glu Met Gly Lys Tyr Ile Lys Ser Phe Val Glu Arg Val Leu Lys
                325                 330                 335

Asn Glu Gln
```

<210> SEQ ID NO 11
<211> LENGTH: 1271
<212> TYPE: DNA
<213> ORGANISM: Artificial Sequence
<220> FEATURE:
<221> NAME/KEY: CDS
<222> LOCATION: (1)..(1017)
<223> OTHER INFORMATION: DNA encoding pre-protein form of secreted
      Renilla luciferase having a cysteine to alanine substitution
      at position 101

<400> SEQUENCE: 11

```
atg tac agg atg caa ctc ctg tct tgc att gca cta agt ctt gca ctt      48
Met Tyr Arg Met Gln Leu Leu Ser Cys Ile Ala Leu Ser Leu Ala Leu
 1               5                  10                  15 gtc aca aac agt gca cct act gaa ttc agc tta aag atg act tcg aaa      96
Val Thr Asn Ser Ala Pro Thr Glu Phe Ser Leu Lys Met Thr Ser Lys
            20                  25                  30 gtt tat gat cca gaa caa agg aaa cgg atg ata act ggt ccg cag tgg     144
Val Tyr Asp Pro Glu Gln Arg Lys Arg Met Ile Thr Gly Pro Gln Trp
```

```
                       35                      40                       45
tgg gcc aga tgt aaa caa atg aat gtt ctt gat tca ttt att aat tat       192
Trp Ala Arg Cys Lys Gln Met Asn Val Leu Asp Ser Phe Ile Asn Tyr
 50                  55                      60 tat gat tca gaa aaa cat gca gaa aat gct gtt att ttt tta cat ggt       240
Tyr Asp Ser Glu Lys His Ala Glu Asn Ala Val Ile Phe Leu His Gly
 65                  70                      75                  80 aac gcg gcc tct tct tat tta tgg cga cat gtt gtg cca cat att gag       288
Asn Ala Ala Ser Ser Tyr Leu Trp Arg His Val Val Pro His Ile Glu
                     85                      90                  95 cca gta gcg cgg gct att ata cca gat ctt att ggt atg ggc aaa tca       336
Pro Val Ala Arg Ala Ile Ile Pro Asp Leu Ile Gly Met Gly Lys Ser
                100                     105                 110 ggc aaa tct ggt aat ggt tct tat agg tta ctt gat cat tac aaa tat       384
Gly Lys Ser Gly Asn Gly Ser Tyr Arg Leu Leu Asp His Tyr Lys Tyr
            115                     120                 125 ctt act gca tgg ttt gaa ctt ctt aat tta cca aag aag atc att ttt       432
Leu Thr Ala Trp Phe Glu Leu Leu Asn Leu Pro Lys Lys Ile Ile Phe
        130                     135                 140 gtc ggc cat gat tgg ggt gct tgt ttg gca ttt cat tat agc tat gag       480
Val Gly His Asp Trp Gly Ala Cys Leu Ala Phe His Tyr Ser Tyr Glu
145                 150                     155                 160 cat caa gat aag atc aaa gca ata gtt cac gct gaa agt gta gta gat       528
His Gln Asp Lys Ile Lys Ala Ile Val His Ala Glu Ser Val Val Asp
                165                     170                 175 gtg att gaa tca tgg gat gaa tgg cct gat att gaa gaa gat att gcg       576
Val Ile Glu Ser Trp Asp Glu Trp Pro Asp Ile Glu Glu Asp Ile Ala
            180                     185                 190 ttg atc aaa tct gaa gaa gga gaa aaa atg gtt ttg gag aat aac ttc       624
Leu Ile Lys Ser Glu Glu Gly Glu Lys Met Val Leu Glu Asn Asn Phe
        195                     200                 205 ttc gtg gaa acc atg ttg cca tca aaa atc atg aga aag tta gaa cca       672
Phe Val Glu Thr Met Leu Pro Ser Lys Ile Met Arg Lys Leu Glu Pro
    210                     215                 220 gaa gaa ttt gca gca tat ctt gaa cca ttc aaa gag aaa ggt gaa gtt       720
Glu Glu Phe Ala Ala Tyr Leu Glu Pro Phe Lys Glu Lys Gly Glu Val
225                 230                     235                 240 cgt cgt cca aca tta tca tgg cct cgt gaa atc ccg tta gta aaa ggt       768
Arg Arg Pro Thr Leu Ser Trp Pro Arg Glu Ile Pro Leu Val Lys Gly
                245                     250                 255 ggt aaa cct gac gtt gta caa att gtt agg aat tat aat gct tat cta       816
Gly Lys Pro Asp Val Val Gln Ile Val Arg Asn Tyr Asn Ala Tyr Leu
            260                     265                 270 cgt gca agt gat gat tta cca aaa atg ttt att gaa tcg gat cca gga       864
Arg Ala Ser Asp Asp Leu Pro Lys Met Phe Ile Glu Ser Asp Pro Gly
        275                     280                 285 ttc ttt tcc aat gct att gtt gaa ggc gcc aag aag ttt cct aat act       912
Phe Phe Ser Asn Ala Ile Val Glu Gly Ala Lys Lys Phe Pro Asn Thr
    290                     295                 300 gaa ttt gtc aaa gta aaa ggt ctt cat ttt tcg caa gaa gat gca cct       960
Glu Phe Val Lys Val Lys Gly Leu His Phe Ser Gln Glu Asp Ala Pro
305                 310                     315                 320 gat gaa atg gga aaa tat atc aaa tcg ttc gtt gag cga gtt ctc aaa      1008
Asp Glu Met Gly Lys Tyr Ile Lys Ser Phe Val Glu Arg Val Leu Lys
                325                     330                 335 aat gaa caa taattacttt ggtttttat ttacatttt cccgggttta               1057
Asn Glu Gln ataatataaa tgtcattttc aacaatttta ttttaactga atatttcaca gggaacattc   1117
```

```
atatatgttg attaatttag ctcgaacttt actctgtcat atcattttgg aatattaacct    1177 ctttcaatga aactttataa acagtggttc aattaattaa tatatattat aattacattt    1237
gttatgtaat aaactcggtt ttattataaa aaaa                                 1271
```

<210> SEQ ID NO 12
<211> LENGTH: 339
<212> TYPE: PRT
<213> ORGANISM: Artificial Sequence
<220> FEATURE:
<223> OTHER INFORMATION: pre-protein form of secreted Renilla luciferase
      having a cysteine to alanine substitution at position 101

<400> SEQUENCE: 12

```
Met Tyr Arg Met Gln Leu Leu Ser Cys Ile Ala Leu Ser Leu Ala Leu
1               5                   10                  15

Val Thr Asn Ser Ala Pro Thr Glu Phe Ser Leu Lys Met Thr Ser Lys
            20                  25                  30

Val Tyr Asp Pro Glu Gln Arg Lys Arg Met Ile Thr Gly Pro Gln Trp
        35                  40                  45

Trp Ala Arg Cys Lys Gln Met Asn Val Leu Asp Ser Phe Ile Asn Tyr
    50                  55                  60

Tyr Asp Ser Glu Lys His Ala Glu Asn Ala Val Ile Phe Leu His Gly
65                  70                  75                  80

Asn Ala Ala Ser Ser Tyr Leu Trp Arg His Val Val Pro His Ile Glu
                85                  90                  95

Pro Val Ala Arg Ala Ile Ile Pro Asp Leu Ile Gly Met Gly Lys Ser
            100                 105                 110

Gly Lys Ser Gly Asn Gly Ser Tyr Arg Leu Leu Asp His Tyr Lys Tyr
        115                 120                 125

Leu Thr Ala Trp Phe Glu Leu Leu Asn Leu Pro Lys Lys Ile Ile Phe
    130                 135                 140

Val Gly His Asp Trp Gly Ala Cys Leu Ala Phe His Tyr Ser Tyr Glu
145                 150                 155                 160

His Gln Asp Lys Ile Lys Ala Ile Val His Ala Glu Ser Val Val Asp
                165                 170                 175

Val Ile Glu Ser Trp Asp Glu Trp Pro Asp Ile Glu Glu Asp Ile Ala
            180                 185                 190

Leu Ile Lys Ser Glu Glu Gly Glu Lys Met Val Leu Glu Asn Asn Phe
        195                 200                 205

Phe Val Glu Thr Met Leu Pro Ser Lys Ile Met Arg Lys Leu Glu Pro
    210                 215                 220

Glu Glu Phe Ala Ala Tyr Leu Glu Pro Phe Lys Glu Lys Gly Glu Val
225                 230                 235                 240

Arg Arg Pro Thr Leu Ser Trp Pro Arg Glu Ile Pro Leu Val Lys Gly
                245                 250                 255

Gly Lys Pro Asp Val Val Gln Ile Val Arg Asn Tyr Asn Ala Tyr Leu
            260                 265                 270

Arg Ala Ser Asp Asp Leu Pro Lys Met Phe Ile Glu Ser Asp Pro Gly
        275                 280                 285

Phe Phe Ser Asn Ala Ile Val Glu Gly Ala Lys Lys Phe Pro Asn Thr
    290                 295                 300

Glu Phe Val Lys Val Lys Gly Leu His Phe Ser Gln Glu Asp Ala Pro
305                 310                 315                 320

Asp Glu Met Gly Lys Tyr Ile Lys Ser Phe Val Glu Arg Val Leu Lys
                325                 330                 335
```

Asn Glu Gln

<210> SEQ ID NO 13
<211> LENGTH: 1271
<212> TYPE: DNA
<213> ORGANISM: Artificial Sequence
<220> FEATURE:
<221> NAME/KEY: CDS
<222> LOCATION: (1)..(1017)
<223> OTHER INFORMATION: DNA encoding pre-protein form of secreted
      Renilla luciferase having a cysteine to alanine substitution
      at position 152

<400> SEQUENCE: 13

| | | | | | | | | | | | | | | | | |
|---|---|---|---|---|---|---|---|---|---|---|---|---|---|---|---|---|
| atg | tac | agg | atg | caa | ctc | ctg | tct | tgc | att | gca | cta | agt | ctt | gca | ctt | 48 |
| Met | Tyr | Arg | Met | Gln | Leu | Leu | Ser | Cys | Ile | Ala | Leu | Ser | Leu | Ala | Leu | |
| 1 | | | | 5 | | | | | 10 | | | | | 15 | | |
| gtc | aca | aac | agt | gca | cct | act | gaa | ttc | agc | tta | aag | atg | act | tcg | aaa | 96 |
| Val | Thr | Asn | Ser | Ala | Pro | Thr | Glu | Phe | Ser | Leu | Lys | Met | Thr | Ser | Lys | |
| | | | 20 | | | | | 25 | | | | | 30 | | | |
| gtt | tat | gat | cca | gaa | caa | agg | aaa | cgg | atg | ata | act | ggt | ccg | cag | tgg | 144 |
| Val | Tyr | Asp | Pro | Glu | Gln | Arg | Lys | Arg | Met | Ile | Thr | Gly | Pro | Gln | Trp | |
| | | 35 | | | | | 40 | | | | | 45 | | | | |
| tgg | gcc | aga | tgt | aaa | caa | atg | aat | gtt | ctt | gat | tca | ttt | att | aat | tat | 192 |
| Trp | Ala | Arg | Cys | Lys | Gln | Met | Asn | Val | Leu | Asp | Ser | Phe | Ile | Asn | Tyr | |
| 50 | | | | | 55 | | | | | 60 | | | | | | |
| tat | gat | tca | gaa | aaa | cat | gca | gaa | aat | gct | gtt | att | ttt | tta | cat | ggt | 240 |
| Tyr | Asp | Ser | Glu | Lys | His | Ala | Glu | Asn | Ala | Val | Ile | Phe | Leu | His | Gly | |
| 65 | | | | | 70 | | | | | 75 | | | | | 80 | |
| aac | gcg | gcc | tct | tct | tat | tta | tgg | cga | cat | gtt | gtg | cca | cat | att | gag | 288 |
| Asn | Ala | Ala | Ser | Ser | Tyr | Leu | Trp | Arg | His | Val | Val | Pro | His | Ile | Glu | |
| | | | | 85 | | | | | 90 | | | | | 95 | | |
| cca | gta | gcg | cgg | tgt | att | ata | cca | gat | ctt | att | ggt | atg | ggc | aaa | tca | 336 |
| Pro | Val | Ala | Arg | Cys | Ile | Ile | Pro | Asp | Leu | Ile | Gly | Met | Gly | Lys | Ser | |
| | | | 100 | | | | | 105 | | | | | 110 | | | |
| ggc | aaa | tct | ggt | aat | ggt | tct | tat | agg | tta | ctt | gat | cat | tac | aaa | tat | 384 |
| Gly | Lys | Ser | Gly | Asn | Gly | Ser | Tyr | Arg | Leu | Leu | Asp | His | Tyr | Lys | Tyr | |
| | | 115 | | | | | 120 | | | | | 125 | | | | |
| ctt | act | gca | tgg | ttt | gaa | ctt | ctt | aat | tta | cca | aag | aag | atc | att | ttt | 432 |
| Leu | Thr | Ala | Trp | Phe | Glu | Leu | Leu | Asn | Leu | Pro | Lys | Lys | Ile | Ile | Phe | |
| | 130 | | | | | 135 | | | | | 140 | | | | | |
| gtc | ggc | cat | gat | tgg | ggt | gct | gct | ttg | gca | ttt | cat | tat | agc | tat | gag | 480 |
| Val | Gly | His | Asp | Trp | Gly | Ala | Ala | Leu | Ala | Phe | His | Tyr | Ser | Tyr | Glu | |
| 145 | | | | | 150 | | | | | 155 | | | | | 160 | |
| cat | caa | gat | aag | atc | aaa | gca | ata | gtt | cac | gct | gaa | agt | gta | gta | gat | 528 |
| His | Gln | Asp | Lys | Ile | Lys | Ala | Ile | Val | His | Ala | Glu | Ser | Val | Val | Asp | |
| | | | | 165 | | | | | 170 | | | | | 175 | | |
| gtg | att | gaa | tca | tgg | gat | gaa | tgg | cct | gat | att | gaa | gaa | gat | att | gcg | 576 |
| Val | Ile | Glu | Ser | Trp | Asp | Glu | Trp | Pro | Asp | Ile | Glu | Glu | Asp | Ile | Ala | |
| | | | 180 | | | | | 185 | | | | | 190 | | | |
| ttg | atc | aaa | tct | gaa | gaa | gga | gaa | aaa | atg | gtt | ttg | gag | aat | aac | ttc | 624 |
| Leu | Ile | Lys | Ser | Glu | Glu | Gly | Glu | Lys | Met | Val | Leu | Glu | Asn | Asn | Phe | |
| | | 195 | | | | | 200 | | | | | 205 | | | | |
| ttc | gtg | gaa | acc | atg | ttg | cca | tca | aaa | atc | atg | aga | aag | tta | gaa | cca | 672 |
| Phe | Val | Glu | Thr | Met | Leu | Pro | Ser | Lys | Ile | Met | Arg | Lys | Leu | Glu | Pro | |
| | 210 | | | | | 215 | | | | | 220 | | | | | |
| gaa | gaa | ttt | gca | gca | tat | ctt | gaa | cca | ttc | aaa | gag | aaa | ggt | gaa | gtt | 720 |
| Glu | Glu | Phe | Ala | Ala | Tyr | Leu | Glu | Pro | Phe | Lys | Glu | Lys | Gly | Glu | Val | |
| 225 | | | | | 230 | | | | | 235 | | | | | 240 | |
| cgt | cgt | cca | aca | tta | tca | tgg | cct | cgt | gaa | atc | ccg | tta | gta | aaa | ggt | 768 |
| Arg | Arg | Pro | Thr | Leu | Ser | Trp | Pro | Arg | Glu | Ile | Pro | Leu | Val | Lys | Gly | |

-continued

```
                 245                 250                 255
ggt aaa cct gac gtt gta caa att gtt agg aat tat aat gct tat cta    816
Gly Lys Pro Asp Val Val Gln Ile Val Arg Asn Tyr Asn Ala Tyr Leu
        260                 265                 270 cgt gca agt gat gat tta cca aaa atg ttt att gaa tcg gat cca gga    864
Arg Ala Ser Asp Asp Leu Pro Lys Met Phe Ile Glu Ser Asp Pro Gly
    275                 280                 285 ttc ttt tcc aat gct att gtt gaa ggc gcc aag aag ttt cct aat act    912
Phe Phe Ser Asn Ala Ile Val Glu Gly Ala Lys Lys Phe Pro Asn Thr
290                 295                 300 gaa ttt gtc aaa gta aaa ggt ctt cat ttt tcg caa gaa gat gca cct    960
Glu Phe Val Lys Val Lys Gly Leu His Phe Ser Gln Glu Asp Ala Pro
305                 310                 315                 320 gat gaa atg gga aaa tat atc aaa tcg ttc gtt gag cga gtt ctc aaa   1008
Asp Glu Met Gly Lys Tyr Ile Lys Ser Phe Val Glu Arg Val Leu Lys
                325                 330                 335 aat gaa caa taattacttt ggttttttat ttacatttt cccgggttta            1057
Asn Glu Gln ataaataaa tgtcattttc aacaatttta ttttaactga atatttcaca gggaacattc   1117
atatatgttg attaatttag ctcgaacttt actctgtcat atcattttgg aatattacct  1177
ctttcaatga aactttataa acagtggttc aattaattaa tatatattat aattacattt  1237
gttatgtaat aaactcggtt ttattataaa aaaa                              1271
```

<210> SEQ ID NO 14
<211> LENGTH: 339
<212> TYPE: PRT
<213> ORGANISM: Artificial Sequence
<220> FEATURE:
<223> OTHER INFORMATION: pre-protein form of secreted Renilla luciferase having a cysteine to alanine substitution at position 152

<400> SEQUENCE: 14

```
Met Tyr Arg Met Gln Leu Leu Ser Cys Ile Ala Leu Ser Leu Ala Leu
1               5                   10                  15

Val Thr Asn Ser Ala Pro Thr Glu Phe Ser Leu Lys Met Thr Ser Lys
            20                  25                  30

Val Tyr Asp Pro Glu Gln Arg Lys Arg Met Ile Thr Gly Pro Gln Trp
        35                  40                  45

Trp Ala Arg Cys Lys Gln Met Asn Val Leu Asp Ser Phe Ile Asn Tyr
    50                  55                  60

Tyr Asp Ser Glu Lys His Ala Glu Asn Ala Val Ile Phe Leu His Gly
65                  70                  75                  80

Asn Ala Ala Ser Ser Tyr Leu Trp Arg His Val Pro His Ile Glu
                85                  90                  95

Pro Val Ala Arg Cys Ile Ile Pro Asp Leu Ile Gly Met Gly Lys Ser
            100                 105                 110

Gly Lys Ser Gly Asn Gly Ser Tyr Arg Leu Leu Asp His Tyr Lys Tyr
        115                 120                 125

Leu Thr Ala Trp Phe Glu Leu Leu Asn Leu Pro Lys Ile Ile Phe
    130                 135                 140

Val Gly His Asp Trp Gly Ala Ala Leu Ala Phe His Tyr Ser Tyr Glu
145                 150                 155                 160

His Gln Asp Lys Ile Lys Ala Ile Val His Ala Glu Ser Val Val Asp
                165                 170                 175

Val Ile Glu Ser Trp Asp Glu Trp Pro Asp Ile Glu Glu Asp Ile Ala
            180                 185                 190
```

-continued

```
Leu Ile Lys Ser Glu Glu Gly Lys Met Val Leu Glu Asn Asn Phe
        195                 200                 205

Phe Val Glu Thr Met Leu Pro Ser Lys Ile Met Arg Lys Leu Glu Pro
    210                 215                 220

Glu Glu Phe Ala Ala Tyr Leu Glu Pro Phe Lys Glu Lys Gly Glu Val
225                 230                 235                 240

Arg Arg Pro Thr Leu Ser Trp Pro Arg Glu Ile Pro Leu Val Lys Gly
                245                 250                 255

Gly Lys Pro Asp Val Val Gln Ile Val Arg Asn Tyr Asn Ala Tyr Leu
                260                 265                 270

Arg Ala Ser Asp Asp Leu Pro Lys Met Phe Ile Glu Ser Asp Pro Gly
            275                 280                 285

Phe Phe Ser Asn Ala Ile Val Glu Gly Ala Lys Lys Phe Pro Asn Thr
290                 295                 300

Glu Phe Val Lys Val Lys Gly Leu His Phe Ser Gln Glu Asp Ala Pro
305                 310                 315                 320

Asp Glu Met Gly Lys Tyr Ile Lys Ser Phe Val Glu Arg Val Leu Lys
                325                 330                 335

Asn Glu Gln

<210> SEQ ID NO 15
<211> LENGTH: 1271
<212> TYPE: DNA
<213> ORGANISM: Artificial Sequence
<220> FEATURE:
<221> NAME/KEY: CDS
<222> LOCATION: (1)..(1017)
<223> OTHER INFORMATION: DNA encoding pre-protein form of secreted
      Renilla luciferase having a cysteine to alanine substitutions at
      positions 52, 101 and 152

<400> SEQUENCE: 15 atg tac agg atg caa ctc ctg tct tgc att gca cta agt ctt gca ctt      48
Met Tyr Arg Met Gln Leu Leu Ser Cys Ile Ala Leu Ser Leu Ala Leu
1               5                   10                  15 gtc aca aac agt gca cct act gaa ttc agc tta aag atg act tcg aaa      96
Val Thr Asn Ser Ala Pro Thr Glu Phe Ser Leu Lys Met Thr Ser Lys
                20                  25                  30 gtt tat gat cca gaa caa agg aaa cgg atg ata act ggt ccg cag tgg     144
Val Tyr Asp Pro Glu Gln Arg Lys Arg Met Ile Thr Gly Pro Gln Trp
            35                  40                  45 tgg gcc aga gct aaa caa atg aat gtt ctt gat tca ttt att aat tat     192
Trp Ala Arg Ala Lys Gln Met Asn Val Leu Asp Ser Phe Ile Asn Tyr
    50                  55                  60 tat gat tca gaa aaa cat gca gaa aat gct gtt att ttt tta cat ggt     240
Tyr Asp Ser Glu Lys His Ala Glu Asn Ala Val Ile Phe Leu His Gly
65                  70                  75                  80 aac gcg gcc tct tct tat tta tgg cga cat gtt gtg cca cat att gag     288
Asn Ala Ala Ser Ser Tyr Leu Trp Arg His Val Val Pro His Ile Glu
                85                  90                  95 cca gta gcg cgg gct att ata cca gat ctt att ggt atg ggc aaa tca     336
Pro Val Ala Arg Ala Ile Ile Pro Asp Leu Ile Gly Met Gly Lys Ser
            100                 105                 110 ggc aaa tct ggt aat ggt tct tat agg tta ctt gat cat tac aaa tat     384
Gly Lys Ser Gly Asn Gly Ser Tyr Arg Leu Leu Asp His Tyr Lys Tyr
        115                 120                 125 ctt act gca tgg ttt gaa ctt ctt aat tta cca aag aag atc att ttt     432
Leu Thr Ala Trp Phe Glu Leu Leu Asn Leu Pro Lys Lys Ile Ile Phe
    130                 135                 140
```

```
gtc ggc cat gat tgg ggt gct gct ttg gca ttt cat tat agc tat gag    480
Val Gly His Asp Trp Gly Ala Ala Leu Ala Phe His Tyr Ser Tyr Glu
145                 150                 155                 160 cat caa gat aag atc aaa gca ata gtt cac gct gaa agt gta gta gat    528
His Gln Asp Lys Ile Lys Ala Ile Val His Ala Glu Ser Val Val Asp
                165                 170                 175 gtg att gaa tca tgg gat gaa tgg cct gat att gaa gaa gat att gcg    576
Val Ile Glu Ser Trp Asp Glu Trp Pro Asp Ile Glu Glu Asp Ile Ala
            180                 185                 190 ttg atc aaa tct gaa gaa gga gaa aaa atg gtt ttg gag aat aac ttc    624
Leu Ile Lys Ser Glu Glu Gly Glu Lys Met Val Leu Glu Asn Asn Phe
        195                 200                 205 ttc gtg gaa acc atg ttg cca tca aaa atc atg aga aag tta gaa cca    672
Phe Val Glu Thr Met Leu Pro Ser Lys Ile Met Arg Lys Leu Glu Pro
    210                 215                 220 gaa gaa ttt gca gca tat ctt gaa cca ttc aaa gag aaa ggt gaa gtt    720
Glu Glu Phe Ala Ala Tyr Leu Glu Pro Phe Lys Glu Lys Gly Glu Val
225                 230                 235                 240 cgt cgt cca aca tta tca tgg cct cgt gaa atc ccg tta gta aaa ggt    768
Arg Arg Pro Thr Leu Ser Trp Pro Arg Glu Ile Pro Leu Val Lys Gly
                245                 250                 255 ggt aaa cct gac gtt gta caa att gtt agg aat tat aat gct tat cta    816
Gly Lys Pro Asp Val Val Gln Ile Val Arg Asn Tyr Asn Ala Tyr Leu
            260                 265                 270 cgt gca agt gat gat tta cca aaa atg ttt att gaa tcg gat cca gga    864
Arg Ala Ser Asp Asp Leu Pro Lys Met Phe Ile Glu Ser Asp Pro Gly
        275                 280                 285 ttc ttt tcc aat gct att gtt gaa ggc gcc aag aag ttt cct aat act    912
Phe Phe Ser Asn Ala Ile Val Glu Gly Ala Lys Lys Phe Pro Asn Thr
    290                 295                 300 gaa ttt gtc aaa gta aaa ggt ctt cat ttt tcg caa gaa gat gca cct    960
Glu Phe Val Lys Val Lys Gly Leu His Phe Ser Gln Glu Asp Ala Pro
305                 310                 315                 320 gat gaa atg gga aaa tat atc aaa tcg ttc gtt gag cga gtt ctc aaa   1008
Asp Glu Met Gly Lys Tyr Ile Lys Ser Phe Val Glu Arg Val Leu Lys
                325                 330                 335 aat gaa caa taattactttt ggttttttat ttacattttt cccgggttta          1057
Asn Glu Gln ataatataaa tgtcattttc aacaatttta ttttaactga atatttcaca gggaacattc  1117
atatatgttg attaatttag ctcgaacttt actctgtcat atcattttgg aatattacct  1177 cttttcaatga aactttataa acagtggttc aattaattaa tatatattat aattacattt  1237
gttatgtaat aaactcggtt ttattataaa aaaa                              1271

<210> SEQ ID NO 16
<211> LENGTH: 339
<212> TYPE: PRT
<213> ORGANISM: Artificial Sequence
<220> FEATURE:
<223> OTHER INFORMATION: pre-protein form of secreted Renilla luciferase
      having a cysteine to alanine substitutions at positions 52, 101
      and 152

<400> SEQUENCE: 16

Met Tyr Arg Met Gln Leu Leu Ser Cys Ile Ala Leu Ser Leu Ala Leu
1               5                   10                  15

Val Thr Asn Ser Ala Pro Thr Glu Phe Ser Leu Lys Met Thr Ser Lys
            20                  25                  30

Val Tyr Asp Pro Glu Gln Arg Lys Arg Met Ile Thr Gly Pro Gln Trp
```

```
                    35                  40                  45
Trp Ala Arg Ala Lys Gln Met Asn Val Leu Asp Ser Phe Ile Asn Tyr
    50                  55                  60

Tyr Asp Ser Glu Lys His Ala Glu Asn Ala Val Ile Phe Leu His Gly
65                  70                  75                  80

Asn Ala Ala Ser Ser Tyr Leu Trp Arg His Val Val Pro His Ile Glu
                85                  90                  95

Pro Val Ala Arg Ala Ile Ile Pro Asp Leu Ile Gly Met Gly Lys Ser
            100                 105                 110

Gly Lys Ser Gly Asn Gly Ser Tyr Arg Leu Leu Asp His Tyr Lys Tyr
        115                 120                 125

Leu Thr Ala Trp Phe Glu Leu Leu Asn Leu Pro Lys Lys Ile Ile Phe
    130                 135                 140

Val Gly His Asp Trp Gly Ala Ala Leu Ala Phe His Tyr Ser Tyr Glu
145                 150                 155                 160

His Gln Asp Lys Ile Lys Ala Ile Val His Ala Glu Ser Val Val Asp
                165                 170                 175

Val Ile Glu Ser Trp Asp Glu Trp Pro Asp Ile Glu Glu Asp Ile Ala
            180                 185                 190

Leu Ile Lys Ser Glu Glu Gly Glu Lys Met Val Leu Glu Asn Asn Phe
        195                 200                 205

Phe Val Glu Thr Met Leu Pro Ser Lys Ile Met Arg Lys Leu Glu Pro
    210                 215                 220

Glu Glu Phe Ala Ala Tyr Leu Glu Pro Phe Lys Glu Lys Gly Glu Val
225                 230                 235                 240

Arg Arg Pro Thr Leu Ser Trp Pro Arg Glu Ile Pro Leu Val Lys Gly
                245                 250                 255

Gly Lys Pro Asp Val Val Gln Ile Val Arg Asn Tyr Asn Ala Tyr Leu
            260                 265                 270

Arg Ala Ser Asp Asp Leu Pro Lys Met Phe Ile Glu Ser Asp Pro Gly
        275                 280                 285

Phe Phe Ser Asn Ala Ile Val Glu Gly Ala Lys Lys Phe Pro Asn Thr
    290                 295                 300

Glu Phe Val Lys Val Lys Gly Leu His Phe Ser Gln Glu Asp Ala Pro
305                 310                 315                 320

Asp Glu Met Gly Lys Tyr Ile Lys Ser Phe Val Glu Arg Val Leu Lys
                325                 330                 335

Asn Glu Gln

<210> SEQ ID NO 17
<211> LENGTH: 1467
<212> TYPE: DNA
<213> ORGANISM: Artificial Sequence
<220> FEATURE:
<221> NAME/KEY: CDS
<222> LOCATION: (1)..(1467)
<223> OTHER INFORMATION: DNA encoding a secreted alkaline phosphatase

<400> SEQUENCE: 17 atg ctg ctg ctg ctg ctg ctg ggc ctg agg cta cag ctc tcc ctg        48
Met Leu Leu Leu Leu Leu Leu Gly Leu Arg Leu Gln Leu Ser Leu
1               5                   10                  15 ggc atc atc cca gtt gag gag gag aac ccg gac ttc tgg aac cgc gag    96
Gly Ile Ile Pro Val Glu Glu Glu Asn Pro Asp Phe Trp Asn Arg Glu
            20                  25                  30 gca gcc gag gcc ctg ggt gcc gcc aag aag ctg cag cct gca cag aca   144
```

```
Ala Ala Glu Ala Leu Gly Ala Ala Lys Lys Leu Gln Pro Ala Gln Thr
         35                  40                  45 gcc gcc aag aac ctc atc atc ttc ctg ggc gat ggg atg ggg gtg tct        192
Ala Ala Lys Asn Leu Ile Ile Phe Leu Gly Asp Gly Met Gly Val Ser
 50                  55                  60 acg gtg aca gct gcc agg atc cta aaa ggg cag aag aag gac aaa ctg        240
Thr Val Thr Ala Ala Arg Ile Leu Lys Gly Gln Lys Lys Asp Lys Leu
 65                  70                  75                  80 ggg cct gag ata ccc ctg gcc atg gac cgc ttc cca tat gtg gct ctg        288
Gly Pro Glu Ile Pro Leu Ala Met Asp Arg Phe Pro Tyr Val Ala Leu
                 85                  90                  95 tcc aag aca tac aat gta gac aaa cat gtg cca gac agt gga gcc aca        336
Ser Lys Thr Tyr Asn Val Asp Lys His Val Pro Asp Ser Gly Ala Thr
            100                 105                 110 gcc acg gcc tac ctg tgc ggg gtc aag ggc aac ttc cag acc att ggc        384
Ala Thr Ala Tyr Leu Cys Gly Val Lys Gly Asn Phe Gln Thr Ile Gly
        115                 120                 125 ttg agt gca gcc gcc cgc ttt aac cag tgc aac acg aca cgc ggc aac        432
Leu Ser Ala Ala Ala Arg Phe Asn Gln Cys Asn Thr Thr Arg Gly Asn
130                 135                 140 gag gtc atc tcc gtg atg aat cgg gcc aag aaa gca ggg aag tca gtg        480
Glu Val Ile Ser Val Met Asn Arg Ala Lys Lys Ala Gly Lys Ser Val
145                 150                 155                 160 gga gtg gta acc acc aca cga gtg cag cac gcc tcg cca gcc ggc acc        528
Gly Val Val Thr Thr Thr Arg Val Gln His Ala Ser Pro Ala Gly Thr
                165                 170                 175 tac gcc cac acg gtg aac cgc aac tgg tac tcg gac gcc gac gtg cct        576
Tyr Ala His Thr Val Asn Arg Asn Trp Tyr Ser Asp Ala Asp Val Pro
            180                 185                 190 gcc tcg gcc cgc cag gag ggg tgc cag gac atc gct acg cag ctc atc        624
Ala Ser Ala Arg Gln Glu Gly Cys Gln Asp Ile Ala Thr Gln Leu Ile
        195                 200                 205 tcc aac atg gac att gac gtg atc cta ggt gga ggc cga aag tac atg        672
Ser Asn Met Asp Ile Asp Val Ile Leu Gly Gly Gly Arg Lys Tyr Met
210                 215                 220 ttt cgc atg gga acc cca gac cct gag tac cca gat gac tac agc caa        720
Phe Arg Met Gly Thr Pro Asp Pro Glu Tyr Pro Asp Asp Tyr Ser Gln
225                 230                 235                 240 ggt ggg acc agg ctg gac ggg aag aat ctg gtg cag gaa tgg ctg gcg        768
Gly Gly Thr Arg Leu Asp Gly Lys Asn Leu Val Gln Glu Trp Leu Ala
                245                 250                 255 aag cgc cag ggt gcc cgg tat gtg tgg aac cgc act gag ctc atg cag        816
Lys Arg Gln Gly Ala Arg Tyr Val Trp Asn Arg Thr Glu Leu Met Gln
            260                 265                 270 gct tcc ctg gac ccg tct gtg acc cat ctc atg ggt ctc ttt gag cct        864
Ala Ser Leu Asp Pro Ser Val Thr His Leu Met Gly Leu Phe Glu Pro
        275                 280                 285 gga gac atg aaa tac gag atc cac cga gac tcc aca ctg gac ccc tcc        912
Gly Asp Met Lys Tyr Glu Ile His Arg Asp Ser Thr Leu Asp Pro Ser
290                 295                 300 ctg atg gag atg aca gag gct gcc ctg cgc ctg ctg agc agg aac ccc        960
Leu Met Glu Met Thr Glu Ala Ala Leu Arg Leu Leu Ser Arg Asn Pro
305                 310                 315                 320 cgc ggc ttc ttc ctc ttc gtg gag ggt ggt cgc atc gac cat ggt cat       1008
Arg Gly Phe Phe Leu Phe Val Glu Gly Gly Arg Ile Asp His Gly His
                325                 330                 335 cat gaa agc agg gct tac cgg gca ctg act gag acg atc atg ttc gac       1056
His Glu Ser Arg Ala Tyr Arg Ala Leu Thr Glu Thr Ile Met Phe Asp
            340                 345                 350
```

```
gac gcc att gag agg gcg ggc cag ctc acc agc gag gag gac acg ctg    1104
Asp Ala Ile Glu Arg Ala Gly Gln Leu Thr Ser Glu Glu Asp Thr Leu
        355                 360                 365 agc ctc gtc act gcc gac cac tcc cac gtc ttc tcc ttc gga ggc tac    1152
Ser Leu Val Thr Ala Asp His Ser His Val Phe Ser Phe Gly Gly Tyr
    370                 375                 380 ccc ctg cga ggg agc tcc atc ttc ggg ctg gcc cct ggc aag gcc cgg    1200
Pro Leu Arg Gly Ser Ser Ile Phe Gly Leu Ala Pro Gly Lys Ala Arg
385                 390                 395                 400 gac agg aag gcc tac acg gtc ctc cta tac gga aac ggt cca ggc tat    1248
Asp Arg Lys Ala Tyr Thr Val Leu Leu Tyr Gly Asn Gly Pro Gly Tyr
            405                 410                 415 gtg ctc aag gac ggc gcc cgg ccg gat gtt acc gag agc gag agc ggg    1296
Val Leu Lys Asp Gly Ala Arg Pro Asp Val Thr Glu Ser Glu Ser Gly
        420                 425                 430 agc ccc gag tat cgg cag cag tca gca gtg ccc ctg gac gaa gag acc    1344
Ser Pro Glu Tyr Arg Gln Gln Ser Ala Val Pro Leu Asp Glu Glu Thr
    435                 440                 445 cac gca ggc gag gac gtg gcg gtg ttc gcg cgc ggc ccg cag gcg cac    1392
His Ala Gly Glu Asp Val Ala Val Phe Ala Arg Gly Pro Gln Ala His
450                 455                 460 ctg gtt cac ggc gtg cag gag cag acc ttc ata gcg cac gtc atg gcc    1440
Leu Val His Gly Val Gln Glu Gln Thr Phe Ile Ala His Val Met Ala
465                 470                 475                 480 ttc gcc gcc tgc ctg gag ccc tac acc                                1467
Phe Ala Ala Cys Leu Glu Pro Tyr Thr
                485
```

<210> SEQ ID NO 18
<211> LENGTH: 489
<212> TYPE: PRT
<213> ORGANISM: Artificial Sequence
<220> FEATURE:
<223> OTHER INFORMATION: secreted alkaline phosphatase

<400> SEQUENCE: 18

```
Met Leu Leu Leu Leu Leu Leu Gly Leu Arg Leu Gln Leu Ser Leu
1               5                   10                  15

Gly Ile Ile Pro Val Glu Glu Glu Asn Pro Asp Phe Trp Asn Arg Glu
            20                  25                  30

Ala Ala Glu Ala Leu Gly Ala Ala Lys Lys Leu Gln Pro Ala Gln Thr
        35                  40                  45

Ala Ala Lys Asn Leu Ile Ile Phe Leu Gly Asp Gly Met Gly Val Ser
    50                  55                  60

Thr Val Thr Ala Ala Arg Ile Leu Lys Gly Gln Lys Lys Asp Lys Leu
65                  70                  75                  80

Gly Pro Glu Ile Pro Leu Ala Met Asp Arg Phe Pro Tyr Val Ala Leu
                85                  90                  95

Ser Lys Thr Tyr Asn Val Asp Lys His Val Pro Asp Ser Gly Ala Thr
            100                 105                 110

Ala Thr Ala Tyr Leu Cys Gly Val Lys Gly Asn Phe Gln Thr Ile Gly
        115                 120                 125

Leu Ser Ala Ala Ala Arg Phe Asn Gln Cys Asn Thr Thr Arg Gly Asn
    130                 135                 140

Glu Val Ile Ser Val Met Asn Arg Ala Lys Lys Ala Gly Lys Ser Val
145                 150                 155                 160

Gly Val Val Thr Thr Thr Arg Val Gln His Ala Ser Pro Ala Gly Thr
                165                 170                 175
```

-continued

```
Tyr Ala His Thr Val Asn Arg Asn Trp Tyr Ser Asp Ala Asp Val Pro
            180                 185                 190

Ala Ser Ala Arg Gln Glu Gly Cys Gln Asp Ile Ala Thr Gln Leu Ile
            195                 200                 205

Ser Asn Met Asp Ile Asp Val Ile Leu Gly Gly Arg Lys Tyr Met
    210             215                 220

Phe Arg Met Gly Thr Pro Asp Pro Glu Tyr Pro Asp Asp Tyr Ser Gln
225             230                 235                 240

Gly Gly Thr Arg Leu Asp Gly Lys Asn Leu Val Gln Glu Trp Leu Ala
            245                 250                 255

Lys Arg Gln Gly Ala Arg Tyr Val Trp Asn Arg Thr Glu Leu Met Gln
            260                 265                 270

Ala Ser Leu Asp Pro Ser Val Thr His Leu Met Gly Leu Phe Glu Pro
            275                 280                 285

Gly Asp Met Lys Tyr Glu Ile His Arg Asp Ser Thr Leu Asp Pro Ser
            290                 295                 300

Leu Met Glu Met Thr Glu Ala Ala Leu Arg Leu Leu Ser Arg Asn Pro
305                 310                 315                 320

Arg Gly Phe Phe Leu Phe Val Glu Gly Gly Arg Ile Asp His Gly His
                325                 330                 335

His Glu Ser Arg Ala Tyr Arg Ala Leu Thr Glu Thr Ile Met Phe Asp
            340                 345                 350

Asp Ala Ile Glu Arg Ala Gly Gln Leu Thr Ser Glu Glu Asp Thr Leu
            355                 360                 365

Ser Leu Val Thr Ala Asp His Ser His Val Phe Ser Phe Gly Gly Tyr
    370                 375                 380

Pro Leu Arg Gly Ser Ser Ile Phe Gly Leu Ala Pro Gly Lys Ala Arg
385                 390                 395                 400

Asp Arg Lys Ala Tyr Thr Val Leu Leu Tyr Gly Asn Gly Pro Gly Tyr
            405                 410                 415

Val Leu Lys Asp Gly Ala Arg Pro Asp Val Thr Glu Ser Glu Ser Gly
            420                 425                 430

Ser Pro Glu Tyr Arg Gln Gln Ser Ala Val Pro Leu Asp Glu Glu Thr
    435                 440                 445

His Ala Gly Glu Asp Val Ala Val Phe Ala Arg Gly Pro Gln Ala His
    450                 455                 460

Leu Val His Gly Val Gln Glu Gln Thr Phe Ile Ala His Val Met Ala
465             470                 475                 480

Phe Ala Ala Cys Leu Glu Pro Tyr Thr
                485
```